US012139722B2

(12) United States Patent
O'Brien et al.

(10) Patent No.: US 12,139,722 B2
(45) Date of Patent: Nov. 12, 2024

(54) METHODS FOR GENERATING AND USING ORGANOIDS AND TISSUE THEREIN

(71) Applicant: REGENTS OF THE UNIVERSITY OF MINNESOTA, Minneapolis, MN (US)

(72) Inventors: Timothy D. O'Brien, Cokato, MN (US); Beth Lindborg, St. Paul, MN (US); Amanda Vegoe, Apple Valley, MN (US)

(73) Assignee: REGENTS OF THE UNIVERSITY OF MINNESOTA, Minneapolis, MN (US)

( * ) Notice: Subject to any disclaimer, the term of this patent is extended or adjusted under 35 U.S.C. 154(b) by 0 days.

(21) Appl. No.: 17/344,064

(22) Filed: Jun. 10, 2021

(65) Prior Publication Data
US 2021/0301251 A1 Sep. 30, 2021

Related U.S. Application Data

(63) Continuation of application No. PCT/US2019/067150, filed on Dec. 18, 2019.

(60) Provisional application No. 62/781,858, filed on Dec. 19, 2018.

(51) Int. Cl.
*C12N 5/00* (2006.01)
*C12N 5/077* (2010.01)

(52) U.S. Cl.
CPC ......... *C12N 5/0062* (2013.01); *C12N 5/0655* (2013.01); *C12N 2500/02* (2013.01); *C12N 2501/15* (2013.01); *C12N 2501/155* (2013.01); *C12N 2501/19* (2013.01); *C12N 2501/905* (2013.01)

(58) Field of Classification Search
CPC ........... C12N 5/0062; C12N 5/0655; C12N 2500/02; C12N 2501/15; C12N 2501/155; C12N 2501/19; C12N 2501/905; C12N 2513/00; C12N 2533/80; C12N 5/0619; C12N 5/0622; C12N 2506/45
See application file for complete search history.

(56) References Cited

U.S. PATENT DOCUMENTS

| | | | | |
|---|---|---|---|---|
| 2008/0032380 A1* | 2/2008 | Kleis | ...................... | C12M 23/04 435/243 |
| 2008/0248570 A1* | 10/2008 | Turner | .................. | C12N 5/0671 435/375 |
| 2009/0123430 A1* | 5/2009 | De Sousa | ............ | C12N 5/0662 435/363 |
| 2009/0136559 A1 | 5/2009 | Athanasiou et al. | | |
| 2011/0082549 A1* | 4/2011 | Clarke | ..................... | C12N 5/00 435/29 |
| 2013/0315882 A1* | 11/2013 | Hu | ....................... | C12N 5/0607 424/93.7 |
| 2014/0315300 A1 | 10/2014 | Oh et al. | | |
| 2015/0093428 A1* | 4/2015 | Rosowski | .......... | G01N 33/6887 424/423 |
| 2015/0283303 A1* | 10/2015 | D'Lima | .................. | A61L 27/54 424/93.7 |
| 2017/0145369 A1* | 5/2017 | Poggel | .................. | C12M 21/18 |
| 2018/0305668 A1* | 10/2018 | Gazit | ................... | C12N 5/0696 |
| 2019/0000886 A1 | 1/2019 | Ross | | |
| 2019/0249137 A1* | 8/2019 | Ellis | ..................... | C12N 5/0679 |
| 2019/0390167 A1 | 12/2019 | Ju et al. | | |
| 2020/0147269 A1* | 5/2020 | Roel | .................. | G01N 33/6887 |
| 2021/0038651 A1 | 2/2021 | Smith et al. | | |

FOREIGN PATENT DOCUMENTS

| | | | |
|---|---|---|---|
| EP | 2878664 A1 * | 6/2015 | ............ A01H 4/001 |
| EP | 2753346 | 4/2020 | |
| JP | 2011041472 A * | 3/2011 | |
| KR | 10-2018-0085699 | 7/2018 | |
| KR | 20200064077 | 6/2020 | |
| TW | 201938788 | 10/2019 | |
| WO | 2014/161075 | 10/2014 | |
| WO | 2015/012582 | 1/2015 | |
| WO | 2016/196661 | 12/2016 | |
| WO | 2017/060884 | 4/2017 | |
| WO | WO 2017/115982 A1 | 7/2017 | |
| WO | 2019/032680 | 2/2019 | |
| WO | 2019/045775 | 3/2019 | |
| WO | 2020/004893 | 1/2020 | |
| WO | 2020/132055 | 6/2020 | |

OTHER PUBLICATIONS

Kanade et al. "Effects of low temperature on electrophysiology and mechanophysiology of human induced pluripotent stem cell-derived cardiomyocytes (hiPSC-CMs)." Micro and Nano Systems Letters vol. 9, Article No. 9 (2021) (Year: 2021).*
Matijasevic et al. "Hypothermia Causes a Reversible, p53-Mediated Cell Cycle Arrest in Cultured Fibroblasts." Oncol Res. 1998;10(11-12):605-10. (Year: 1998).*
Kubrova et al. "Hypothermia and nutrient deprivation alter viability of human adipose-derived mesenchymal stem cells."Gene. Jan. 5, 2020;722:144058. (Year: 2020).*
Höpfl et al. "Differentiating embryonic stem cells into embryoid bodies." Methods Mol Biol. 2004;254:79-98 (Year: 2004).*
Millipore Sigma. "Neural Stem Cell FAQs." retrived from https://www.sigmaaldrich.com/US/en/technical-documents/technical-article/cell-culture-and-cell-culture-analysis/stem-cell-culture/neural-stem-cell-faq. Accessed Mar. 4, 2022 (Year: 2022).*

(Continued)

*Primary Examiner* — Titilayo Moloye
(74) *Attorney, Agent, or Firm* — Mueting Raasch Group

(57) ABSTRACT

This disclosure describes methods for organoid generation including, for example, for generation of a multi-tissue organoid. The multi-tissue organoid may include cartilage, bone, epithelium, and/or fibrous connective tissue. This disclosure further describes methods for isolating cells from the organoids and methods of using the organoids and cells of the organoids.

15 Claims, 21 Drawing Sheets

(56) References Cited

OTHER PUBLICATIONS

Bhatia et al. "Microfluidic organs-on-chips." Nature Biotechnology vol. 32, pp. 760-772 (2014) (Year: 2014).*
Adesida et al. "Hypoxia mediated isolation and expansion enhances the chondrogenic capacity of bone marrow mesenchymal stromal cells."Stem Cell Res Ther. Mar. 2, 2012;3(2):9. (Year: 2012).*
Li et al. "Scalable and physiologically relevant microenvironments for human pluripotent stem cell expansion and differentiation." Biofabrication. Feb. 1, 2018;10(2):025006. (Year: 2018).*
Irie et al. "Reconstruction of cartilage tissue using scaffold-free organoid culture technique" Reconstruction of cartilage tissue using scaffold-free organoid culture technique (Year: 2008).*
Liao et al. "Hyaluronan: Pharmaceutical Characterization and Drug Delivery." Drug Deliv. Nov.-Dec. 2005;12(6):327-42. (Year: 2005).*
Zamponi, Martina. "Developmental Steps for a Functional Three-Dimensional Cell Culture System for the Study of Asymmetrical Division of Neural Stem Cells" (Aug. 2018). Master of Science (MS), Thesis, Electrical & Computer Engineering, Old Dominion University (Year: 2018).*
Koay et al. "Hypoxic chondrogenic differentiation of human embryonic stem cells enhances cartilage protein synthesis and biomechanical functionality." Osteoarthritis Cartilage. Dec. 2008;16(12):1450-6. (Year: 2008).*
Medical Definition "Induce." retrived from https://www.merriam-webster.com/dictionary/induce. accessed Apr. 13, 2023 (Year: 2023).*
Yamashita et al., Generation of scaffoldless hyaline cartilaginous tissue from human iPSCs. Stem Cell Reports 4, 404-418 (2015).
Tirkkonen et al., Osteogenic medium is superior to growth factors in differentiation of human adipose stem cells towards bone-forming cells in 3D culture. Eur Cell Mater 25, 144-158 (2013).
Suchorska et al., Gene expression profile in human induced pluripotent stem cells: Chondrogenic differentiation in vitro, part A. Mol Med Rep 15, 2387-2401 (2017).
Solchaga et al., Chondrogenic differentiation of bone marrow-derived mesenchymal stem cells: tips and tricks. Methods Mol Biol 698, 253-278 (2011).
Rosenzweig et al., Thermoreversible hyaluronan-hydrogel and autologous nucleus pulposus cell delivery regenerates human intervertebral discs in an ex vivo, physiological organ culture model. Eur Cell Mater 36, 200-217 (2018).
Pohlig et al., Hyaluronic Acid Suppresses the Expression of Metalloproteinases in Osteoarthritic Cartilage Stimulated Simultaneously by Interleukin 1beta and Mechanical Load. PLoS One 11, e0150020 (2016).
Meinert et al., A novel bioreactor system for biaxial mechanical loading enhances the properties of tissue-engineered human cartilage. Sci Rep 7, 16997 (2017).
Lindborg et al., Rapid Induction of Cerebral Organoids From Human Induced Pluripotent Stem Cells Using a Chemically Defined Hydrogel and Defined Cell Culture Medium. Stem Cells Transl Med 5, 970-979 (2016).
Lietman, Induced pluripotent stem cells in cartilage repair. World J Orthop 7, 149-155 (2016).
Lee et al., Human iPSC-derived chondrocytes mimic juvenile chondrocyte function for the dual advantage of increased proliferation and resistance to IL-1beta. Stem Cell Res Ther 8, 244 (2017).
Ferguson et al., Mapping molecular landmarks of human skeletal ontogeny and pluripotent stem cell-derived articular chondrocytes. Nat Commun 9, 3634 (2018).
Bejoy et al., Differential Effects of Heparin and Hyaluronic Acid on Neural Patterning of Human Induced Pluripotent Stem Cells. ACS Biomater Sci Eng (2018).

Amann et al., Hyaluronic acid facilitates chondrogenesis and matrix deposition of human adipose derived mesenchymal stem cells and human chondrocytes co-cultures. Acta Biomater 52, 130-144 (2017).
Adkar et al., Step-Wise Chondrogenesis of Human Induced Pluripotent Stem Cells and Purification Via a Reporter Allele Generated by CRISPR-Cas9 Genome Editing. Stem Cells 37, 65-76 (2019).
International Search Report and Written Opinion mailed Mar. 24, 2020 for PCT/US2019/067150, 9 pages.
International Preliminary Report on Patentability mailed Jul. 1, 2021 for PCT/US2019/067150, 8 pages.
Adil et al., "Efficient generation of hPSC-derived midbrain dopaminergic neurons in a fully defined, scalable, 3D biomaterial platform" Jan. 2017 Scientific Reports 7(40573):1-11.
PCT/US2018/045775 filed Aug. 8, 2018; International Search Report and Written Opinion issued Oct. 12, 2018; 10 pages.
Sanchez-Danes et al., "Efficient generation of A9 midbrain dopaminergic neurons by lentiviral delivery of LMX1A in human embryonic stem cells and induced pluripotent stem cells" Jan. 2012 Human Gene Therapy 23(1):56-69.
Boehnke et al., "Assay Establishment and Validation of a High-Throughput Screening Platform for Three-Dimensional Patient-Derived Colon Cancer Organoid Cultures," Journal of Biomolecular Screening, vol. 21(9), 2016, pp. 931-941.
Evenou et al., "Gas-Permeable Membranes and Co-Culture with Fibrobalsts Enable High-density Hepatocyte Culture as Multilayered Liver Tissues," American Institute of Chemical Engineers, Vo. 27, No. 4, 2011, pp. 1146-1153.
Kim et al., "Optimizing Seeding and Culture Methods to Engineer Smooth Muscle Tissue on Biodegradable Polymer Matrices," Biotechnology and Bioengineering, vol. 57, No. 1, Jan. 5, 1998, pp. 46-54.
McRitchie et al., "Specific A10 Dopaminergic Nuclei in the Midbrain Degenerate in Parkinson's Disease,", Experimental Neurology, 144, 1997, pp. 202-213.
Sommerville et al., "Bioreactors get personal," Oncoimmunology 1.8, Nov. 2012, pp. 1435-1437.
Sridhar et al., "Covalently tethered TGF-62 1 with encapsulated chondrocytes in a PEG hydrogel system enhances extracellular matrix production," Journal of Biomedical Materials Research A, vol. 102A, Issue 12, Dec. 2014, pp. 4464-4472.
International Search Report and Written Opinion for PCT/US2022/043839, mailed Feb. 2, 2023; 10 pages.
Jo et al., "Midbrain-like Organoids from Human Pluripotent Stem Cells Contain Functional Dopaminergic and Neuromelanin-Producing Neurons" Cell Stem Cell, Vo. 19, Aug. 4, 2016; pp. 248-257.
Qian et al., "Brain-Region-Specific Organoids Using Mini-bioreactors for Modeling ZIKV Exposure" Cell, Vo. 165, May 19, 2016; pp. 1238-1254.
Ekerdt et al., Thermoreversible Hyaluronic Acid-PNIPAAm Hydrogel Systems for 3D Stem Cell Culture *Adv Healthc Mater*. Jun. 2018; 7(12): e1800225.
Gerecht et al., Hyaluronic acid hydrogel for controlled self-renewal and differentiation of human embryonic stem cells *PNAS* Jul. 3, 2007; 104(27):11298-303.
Liu et al., Modified Hyaluronan Hydrogels Support the Maintenance of Mouse Embryonic Stem Cells and Human Induced Pluripotent Stem Cells *Macromol. Biosci* 2012; 12:1034-42.
International Preliminary Report on Patentability mailed Mar. 28, 2024, for International Application No. PCT/US2022/043839. 7 pages.

* cited by examiner

METHODS FOR GENERATING AND USING ORGANOIDS AND TISSUE THEREIN

This application is a continuation application of International Application No. PCT/US2019/067150, filed Dec. 18, 2019, which claims the benefit of U.S. Provisional Application No. 62/781,858, filed Dec. 19, 2018, each of which is incorporated by reference herein in its entirety.

BACKGROUND

Pluripotent stem cells (PSCs), such as induced pluripotent stem cells (iPSCs) or embryonic stem cells (ESCs), can self-organize under various conditions to form complex tissue structures—also known as organoids—that recapitulate important developmental features and structural and functional characteristics typical of particular tissues.

SUMMARY OF THE INVENTION

This disclosure describes methods for organoid generation including, for example, for generation of a multi-tissue organoid (also referred to here in an "MTO") that includes cartilage, bone, fibrous connective tissue, or epithelial tissue, or a combination thereof. In some embodiments, the cartilage includes hyaline cartilage. The cartilage or chondrocytes isolated from the organoid may be used to repair cartilage due to traumatic injury, osteoarthritis, etc.

In one aspect, this disclosure describes a method that includes: introducing an input cell into a cell culture medium including hyaluronic acid; transferring the input cell to a cell culture device; culturing the cell in the cell culture device for at least 1 week; and producing an organoid that includes cartilage, bone, fibrous connective tissue, or epithelial tissue, or a combination thereof. In some embodiments, the method includes culturing the cell under chemically defined conditions.

In some embodiments, the organoid includes a multi-tissue organoid. In some embodiments, the cartilage includes hyaline cartilage. In some embodiments, the organoid includes bone, fibrous connective tissue, or epithelial tissue, or a combination thereof.

In some embodiments, the cell culture medium further includes one or more of chitosan, fibroblast growth factor, transforming growth factor beta (TGFβ), growth differentiation factor 5 (GDF-5), and bone morphogenetic protein 2 (BMP-2).

In some embodiments, the organoid includes one or more of an oligodendrocyte, an astrocyte, a polydendrocyte, a neural precursor cell, a neural stem cell, a neural progenitor cell, a neural crest cell, a chondrocyte, a cytokeratin-expressing epithelial cell, a type 1-collagen-expressing cell, an osteocyte, a mesenchymal stem cell, a skeletal stem cell, a derivative of an oligodendrocyte, a derivative of an astrocyte, a derivative of a polydendrocyte, a derivative of a neural precursor cell, a derivative of a neural stem cell, a derivative of a neural progenitor cell, a derivative of a neural crest cell, a derivative of a chondrocyte, a derivative of a cytokeratin-expressing epithelial cell, a derivative of a type 1-collagen-expressing cell, a derivative of an osteocyte, a derivative of a mesenchymal stem cell, or a derivative of a skeletal stem cell, or a mixture thereof.

In some embodiments, the input cell includes an embryonic stem cell (ESC), an induced pluripotent stem cell (iPSC), or a neural progenitor cell.

In some embodiments, the method includes removing the input cell from a culture plate. Removing the input cell from the culture plate may include, for example, exposing the cell to one or more of a cell dissociation enzyme, a citrate buffer, phosphate buffered saline, and a cell culture media.

In some embodiments, introducing an input cell into a cell culture medium includes introducing the cell into a cell culture matrix. Introducing the cell into the cell culture matrix may include, for example, introducing a single cell, introducing a colony of cells, or introducing an embryoid body.

In some embodiments, transferring the input cell to a cell culture device includes transferring the cell in the cell culture matrix. In some embodiments, at the time of transferring the input cell to a cell culture device, the cell culture matrix may include sections of up to 80 µL, of up to 50 µL, of up to 25 µL, of up to 15 µL, or of up to 10 µL. In some embodiments, at the time of transferring the input cell to a cell culture device, the cell culture matrix may include sections of at least 1 µL. In some embodiments, at the time of transferring the input cell to a cell culture device, the input cell is present in the cell culture matrix at a concentration of at least $7.6 \times 10^5$ cells per 10 µL matrix, at least $1.2 \times 10^6$ cells per 10 µL matrix, or at a concentration of at least $1.4 \times 10^6$ cells per 10 µL matrix. In some embodiments, at the time of transferring the input cell to a cell culture device, the input cell is present in the cell culture matrix at a concentration of up to $3 \times 10^6$ cells per 10 µL matrix.

In some embodiments, the cell culture device includes a second cell culture medium. The second cell culture medium may include, in some embodiments, a serum-free cell culture medium, a feeder-free cell culture medium, an iPSC medium, and/or a neural medium. The second cell culture medium may include, in some embodiments, a neural induction factor, a neural growth factor, or a growth and differentiation factor that promotes formation and maturation of hyaline cartilage, a growth and differentiation factor that promotes formation and maturation of bone, a growth and differentiation factor that promotes formation and maturation of an epithelial cell, or a growth and differentiation factor that promotes formation and maturation of fibrous connective tissue, or a combination thereof.

In some embodiments, the cell culture device may include a bioreactor. In some embodiments, the cell culture device may include a gas permeable membrane surface and/or a silicone surface. In embodiments, wherein the cell culture device includes a silicone surface, the silicone surface can include dimethyl silicone. In some embodiments, wherein the cell culture device includes a gas permeable membrane surface, the method may further include removing the cell from the gas permeable membrane surface.

In some embodiments, culturing the cell in the cell culture device includes culturing the cell at room temperature. In some embodiments, culturing the cell in the cell culture device includes culturing the cell at 37° C. In some embodiments, culturing the cell in the cell culture device includes culturing the cell in hypoxic conditions.

In some embodiments, wherein the method includes introducing the cell into a cell culture matrix the method may further include removing the cell culture matrix from the organoid. The cell culture matrix may be removed using a mechanical method and/or an enzymatic method.

In some embodiments, the method includes dis-aggregating the cells of the organoid to produce a population of individualized cells. In some embodiments, the method may also include culturing a cell from the population of individualized cells.

In some embodiments, the method includes isolating a chondrocyte from the organoid. In some embodiments, the method includes forming a chondrocyte aggregate. In some embodiments, the method includes culturing the chondrocyte on an ultra-low attachment plate or in a chondrogenic media, or both.

In some embodiments, the organoid includes a cell expressing glial fibrillary acidic protein (GFAP); a cell expressing microtubule associated protein 2 (MAP2); and a cell expressing myelin basic protein (MBP); a cell expressing type 1 collagen (T1Col); a cell expressing type 2 collagen (T2Col); a cell expressing aggrecan; or a cell expressing cytokeratins; or a combination thereof.

In another aspect, this disclosure describes an organoid, a cell of the organoid, a tissue of the organoid, a matrix of the organoid, a chondrocyte, and/or a chondrocyte aggregate generated using the methods described herein. The disclosure further describes methods of using the organoid, the cell of the organoid, the tissue of the organoid, the matrix of the organoid, the chondrocyte, and/or the chondrocyte aggregate. For example, the organoid may be used as a source of therapeutic cells including, for example, as a source of hyaline cartilage. In some embodiments, a cell of the organoid may be used for repair of articular cartilage. In some embodiments, the organoid includes bone.

In a further aspect, this disclosure describes cartilage generated using the methods of described herein and methods of using that cartilage. In some embodiments, the cartilage includes hyaline cartilage.

In yet another aspect, this disclosure describes an organoid that includes cartilage. The organoid may further include a cell expressing GFAP, a cell expressing MAP2; a cell expressing MBP; a cell expressing T2Col; a cell expressing aggrecan; or a cell expressing cytokeratins; or a combination thereof. In some embodiments, the cartilage includes hyaline cartilage. In some embodiments, the cartilage includes type 2 collagen (T2Col), aggrecan, chondroitin sulphate, or a chondrocyte, or a combination thereof.

As used herein, an "organoid" contains an organ-specific cell type, is capable of recapitulating a specific function of the organ and contains a cell and/or structure that is spatially organized similar to that organ.

The words "preferred" and "preferably" refer to embodiments of the invention that may afford certain benefits, under certain circumstances. However, other embodiments may also be preferred, under the same or other circumstances. Furthermore, the recitation of one or more preferred embodiments does not imply that other embodiments are not useful, and is not intended to exclude other embodiments from the scope of the invention.

The terms "comprises" and variations thereof do not have a limiting meaning where these terms appear in the description and claims.

Unless otherwise specified, "a," "an," "the," and "at least one" are used interchangeably and mean one or more than one.

Also herein, the recitations of numerical ranges by endpoints include all numbers subsumed within that range (for example, 1 to 5 includes 1, 1.5, 2, 2.75, 3, 3.80, 4, 5, etc.).

For any method disclosed herein that includes discrete steps, the steps may be conducted in any feasible order. And, as appropriate, any combination of two or more steps may be conducted simultaneously.

Unless otherwise indicated, all numbers expressing quantities of components, molecular weights, and so forth used in the specification and claims are to be understood as being modified in all instances by the term "about." Accordingly, unless otherwise indicated to the contrary, the numerical parameters set forth in the specification and claims are approximations that may vary depending upon the desired properties sought to be obtained by the present invention. At the very least, and not as an attempt to limit the doctrine of equivalents to the scope of the claims, each numerical parameter should at least be construed in light of the number of reported significant digits and by applying ordinary rounding techniques.

Notwithstanding that the numerical ranges and parameters setting forth the broad scope of the invention are approximations, the numerical values set forth in the specific examples are reported as precisely as possible. All numerical values, however, inherently contain a range necessarily resulting from the standard deviation found in their respective testing measurements.

All headings are for the convenience of the reader and should not be used to limit the meaning of the text that follows the heading, unless so specified.

The above summary of the present invention is not intended to describe each disclosed embodiment or every implementation of the present invention. The description that follows more particularly exemplifies illustrative embodiments. In several places throughout the application, guidance is provided through lists of examples, which examples can be used in various combinations. In each instance, the recited list serves only as a representative group and should not be interpreted as an exclusive list.

BRIEF DESCRIPTION OF THE FIGURES

FIG. 11A shows current injections evoked action potentials with stable resting membrane potential. FIG. 11B shows an exemplary trace of a cell with spontaneous synaptic activity (likely a mEPSC) in voltage clamp. FIG. 11C shows an exemplary response to 10 μM NMDA, indicating the presence of glutaminergic neurons.

DETAILED DESCRIPTION OF ILLUSTRATIVE EMBODIMENTS

Figure 1A:
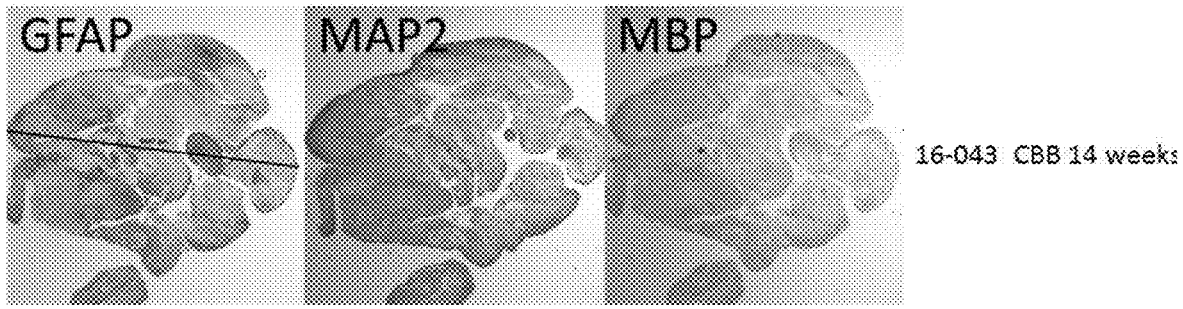
FIG. 1 shows organoids from iPSC lines CS1 and CBB after 8.5-14 weeks of culture in ESSENTIAL 8 medium in GREX 100 cell culture devices. Panel A) Immunohistochemical stains on histologic sections of a large organoid derived from cell line CBB show markers of differentiation to astrocytes (GFAP, glial fibrillar acidic protein), neurons (MAP2, microtubule-associated protein), and oligodendrocytes (MBP, myelin basic protein) in extensive regions. Size bar in first panel=5787 µm. Panel B) Immunohistochemical stains as in panel A on histologic sections of organoids from CS1 and CBB cell lines (15-343=CS1 13 weeks, 16-043=CBB 14 weeks, and 16-009=CBB 8.5 weeks) showing high magnification detail of astrocytes, neurons, and oligodendrocytes. Size bars=50 µm.

This disclosure describes methods for organoid generation including, for example, for generation of an organoid including cartilage. In some embodiments, the cartilage is hyaline cartilage. Surprisingly, as further described herein, a method for generating brain organoids unexpectedly led to the discovery of a method for creating a virtually unlimited source of cartilage (for example, hyaline cartilage). Such cartilage may be used for, for example, repair of articular cartilage due to traumatic injury, osteoarthritis, etc.

In contrast to the prevalent repair modality at the time of the invention (autologous chondrocyte implantation) which requires harvest of normal articular cartilage from the patient and expansion of chondrocytes that are then implanted in the injury site, the methods described herein could provide an off-the-shelf cartilage cell product which would be more cost-effective and would eliminate the need for surgery to harvest cartilage.

In one aspect, this disclosure describes a method that includes: introducing an input cell (for example, an embryonic stem cell (ESC), an induced pluripotent stem cell (iPSC), or a neural progenitor cell) into a cell culture medium including hyaluronic acid; transferring the input cell to a cell culture device; and culturing the cell in the cell culture device for at least 1 week to produce an organoid. In some embodiments, the method produces an organoid including cartilage. In some embodiments, the method produces an organoid including bone. In some embodiments, the method produced an organoid including fibrous connective tissue. In some embodiments, the method produces an organoid including epithelial tissue including, for example, a cytokeratin-expressing epithelial cell. In some embodiments, the method produced an organoid including an osteocyte, a mesenchymal stem cell, and/or a skeletal stem cell.

In contrast to methods for inducing iPSCs to differentiate to cartilage known at the time of the invention (Yamashita et al., Stem Cell Reports 2015; 4:404-418; Lee et al. *Stem Cell Research & Therapy* 2017; 8:244; Suchorska et al. *Molecular Medicine Reports* 2017; 15:2387-2401; Ferguson et al. *Nature Communications* 2018; 9:3634; Adkar et al. *Stem Cells* 2019; 37:65-76), the methods described herein include producing an organoid.

In further contrast to methods for inducing iPSCs to differentiate to cartilage known at the time of the invention, the methods described herein use only chemically defined cell culture components (for example, chemically-defined hydrogel (hyaluronan and chitosan) and/or chemically-defined cell culture medium (E8 or similar media containing FGF2 and/or TGFβ1)) without the use of any xenobiotic materials such as fetal bovine serum or extracellular matrix-like products such as Matrigel.

In some embodiments, including where the method produces an organoid including cartilage, the cartilage includes hyaline cartilage. In some embodiments, hyaline cartilage may be identified by the presence of type 2 collagen (T2Col), aggrecan, chondroitin sulphate, or a chondrocyte, or a combination thereof. In some embodiments, hyaline cartilage may be identified using histological markers. In some embodiments, hyaline cartilage may be identified by detecting the presence of a chondrocyte. A chondrocyte may, in some embodiments, be detected by the protein or gene expression of a marker including, for example, CD9, CD10, CD14, CD26, CD44, CD49a, CD49b, CD49c, CD49e, CD49f, CD51, CD54, CD56 CD58, CD63, CD71, CD81, CD82, CD90, CD95, CD99, CD105, CD106, CD119, CD120a, CD130, CD140a, CD151, CD166, CD221, aggrecan, type II collagen (also referred to as type 2 collagen), type VI collagen, type IX collagen, type X collagen, type XI collagen, annexin A6, SRY-Box 9 (Sox9), matrilin 1, hyaluronan synthase, integral membrane protein 2a, chondroadherin, link protein 1, cathepsin B, cartilage acidic protein 1, or epiphycan, or a combination thereof.

In some embodiments, including where the method produces an organoid including bone, bone may be identified using histological markers. In some embodiments, bone may be identified by protein or gene expression including, for example, expression of osteocalcin, osteonectin, or osteopontin, or a combination thereof.

In some embodiments, including where the method produces an organoid including fibrous connective tissue, fibrous connective tissue may be identified by using histological markers. In some embodiments, fibrous connective tissue may be identified by the presence of type 1 collagen (T1Col) and/or a fibroblast. In some embodiments, fibrous connective tissue and/or a fibroblast may be identified by protein or gene expression including, for example, expression of prolyl-4-hydroxylase, MAS516 antigen, or fibroblast specific protein 1, or a combination thereof.

Input Cells

An input cell may include, for example, an embryonic stem cell (ESC), an induced pluripotent stem cell (iPSC), or a neural progenitor cell. An ESC may include, for example, an H9 cell. An iPSC may include an iPSC cell line. In some embodiments, an iPSC cell line may include a cell line of Table 1. In some embodiments, an iPSC cell line may include CS1, CBB, 1024, or R76.

In some embodiments, the input cell is preferably an undifferentiated iPSC. That is, in contrast to, for example, the methods of WO 2017/060884 which teaches using differentiated neuroepithelial stem cells expressing SOX1, SOX2, PAX6, and NESTIN to generate a midbrain organoid, the input cell of the present disclosure does not need to express and, in some embodiments, may preferably not express neural precursor cell markers (for example, SOX1, SOX2, PAX6, and NESTIN).

In some embodiments, the method may include preparing the input cell and/or removing the input cell from a culture plate. Cells may be removed from a culture plate by any suitable method. For example, the cell may be exposed to one or more of a cell dissociation enzyme, a collagenase, a citrate buffer, phosphate buffered saline (PBS), and a cell culture media. In some embodiments, the cell may be exposed to a cell passaging solution. A cell dissociation enzyme may include, for example, a collagenase, a catalase, a dispase, an elastase, a hyaluronidase, papain, a trypsin, TrypLE (Thermo Fisher Scientific, Waltham, MA), ACCUMAX (Sigma-Aldrich, St. Louis, MO), ACCUTASE (Sigma-Aldrich, St. Louis, MO), etc.

Introducing the Cell into Cell Culture Medium

The method for organoid generation includes introducing the input cell into a cell culture medium including hyaluronic acid. The hyaluronic acid may be cross-linked or non-crosslinked. In some embodiments, the cell culture medium also includes chitosan.

In some embodiments, the cell culture medium includes fibroblast growth factor (also known as bFGF, FGF2 or FGF-β). In some embodiments, the cell culture medium includes a transforming growth factor including, for example, transforming growth factor beta 1 (TGFβ1). In some embodiments, the cell culture medium includes a growth and differentiation factor that promotes formation and maturation of hyaline cartilage including, for example, transforming growth factor beta 1 (TGFβ1), transforming growth factor beta 3 (TGFβ3), growth differentiation factor 5 (GDF-5), or bone morphogenetic protein 2 (BMP-2), etc., or a combination thereof. For example, in some embodiments, the cell culture medium includes GDF-5 or BMP-2 or both. In some embodiments, the cell culture medium includes a growth and differentiation factor that promotes formation and maturation of bone, an epithelial cell, or fibrous connective tissue.

In some embodiments, the cell culture medium does not include a neurotrophin. Exemplary neurotrophins include nerve growth factor (NGF), brain-derived neurotrophic factor (BDNF), neurotrophin-3 (NT-3), neurotrophin-4 (NT-4) as well as GDNF family of ligands and ciliary neurotrophic factor (CNTF). The GDNF family of ligands includes glial cell line-derived neurotrophic factor (GDNF), neurturin (NRTN), artemin (ARTN), and persephin (PSPN).

In some embodiments, the cell culture medium is a solution. In some embodiments, the hyaluronic acid of the cell culture media may be dissolved in the cell culture media. In some embodiments, the hyaluronic acid of the cell culture media may be bonded to a surface.

In some embodiments, the cell culture medium includes a cell culture matrix. In some embodiments, the cell culture matrix includes a hydrogel. In some embodiments, a cell culture medium includes CELL-MATE3D (BRTI Life Sciences, Two Harbors, MN) or Cell-Mate3D μGel 40 (BRTI Life Sciences, Two Harbors, MN). In some embodiments, introducing the input cell into a cell culture matrix includes embedding the cell in the cell culture matrix. In some embodiments, the cell culture medium preferably does not include MATRIGEL (Corning, Corning, NY), CULTREX BME (Trevigen, Inc., Gaithersburg, MD), or other media including tumor-derived basement membrane components. Avoiding the use of media including tumor-derived basement membrane or other undefined components may provide certain advantages because the use of such ill-defined materials can produce significant variability and elicit undefined biological signals.

An input cell may be introduced into the cell culture medium as a single cell, as a colony of cells, as a group of cells, or as a sphere including, for example, as an embryoid body.

Cells may be introduced into the cell culture medium at any suitable concentration. In some embodiments, including for example, when the cell culture medium includes a cell culture matrix, the input cell may be present in the cell culture matrix at a concentration of at least $7.6 \times 10^5$ cells per 10 μL matrix, at least $1.2 \times 10^6$ cells per 10 μL matrix, at least $1.4 \times 10^6$ cells per 10 μL matrix, or at least $1.6 \times 10^6$ cells per 10 µL matrix. In some embodiments, the input cell may be present in the cell culture matrix at a concentration of up to $3\times10^6$ cells per 10 µL matrix.

Without wishing to be bound by theory, it is believed that introducing the cells into a cell culture matrix at a very high concentration (for example, at least $7.6\times10^5$ cells per 10 µL matrix) results in the formation of a matrix with low macroscopic integrity. For example, at $7.6\times10^5$ cells per 10 µL matrix, cells are present at twice the concentration used in Lindborg et al. Stem Cells Translational Medicine, 2016, 5(7):970-979, and the matrix demonstrates significantly less integrity at a macroscopic scale while maintaining association between the cells and matrix components. The resulting low integrity construct undergoes macroscopic dissociation after addition to the cell culture device, yet, despite the loss of macroscopic three-dimensional structure, organoid formation is improved over the use of cell culture matrix with lower concentrations of cells. Moreover, as described below, macroscopic disintegration of the matrix may allow the resulting organoids to emerge from the matrix without manual removal.

Cell Culture Device

After the input cell has been introduced into a cell culture medium including hyaluronic acid, the cell is transferred to a cell culture device.

In some embodiments, transferring the input cell to a cell culture device includes transferring the cell in the cell culture medium.

In some embodiments, transferring the input cell to a cell culture device includes transferring the cell in the cell culture matrix. In some embodiments, including when transferring the input cell to a cell culture device includes transferring the cell in the cell culture matrix, the cell culture matrix includes sections of at least 1 µL, or at least 5 µL, and may include sections of up to 10 µL, up to 15 µL, up to 25 µL, up to 50 µL, or up to 80 µL. In some embodiments, transferring the cell in the cell culture matrix includes transferring at least one input cell per one polyelectrolytic fiber and/or at least one input cell per an unreacted component of the matrix.

In some embodiments, the cell culture conditions-including both the cell culture medium and the cell culture device-include chemically defined conditions. As used herein, chemically defined conditions indicate that neither the cell culture medium or the cell culture device include serum or other animal-derived components. The use of chemically defined conditions prevents drawbacks associated with the use of animal-derived components in the cell culture medium or the cell culture device including inconsistency and contamination.

Cell Culture Devices

A cell culture device may include, for example, a bioreactor, a spinner flask, and a roller bottom flask. In some embodiments, the cell culture device preferably includes a gas permeable membrane surface. A gas permeable membrane may include a silicone surface including, for example a dimethyl silicone surface. The gas permeable membrane may form any suitable surface of the cell culture device including, for example, a bottom surface or a side of a plate or a flask. In some embodiments, the cell culture device may preferably include a GREX cell culture device (Wilson Wolf Corporation, St. Paul, MN).

In some embodiments, including, for example, when the cell culture device include a bioreactor such as the GREX cell culture device, the cell culture device does not need to be agitated.

Second Cell Culture Medium

In some embodiments, the cell culture device includes a second cell culture medium. In some embodiments, the second cell culture medium may include a feeder-free cell culture medium. In some embodiments, the second cell culture medium may include a serum-free cell culture medium. In contrast to other methods at the time of the invention, that typically required the use of fetal bovine serum in the culture medium to promote cartilage differentiation from stem cells, the methods described herein achieve organoids including cartilage without the use of serum in the cell culture medium.

In some embodiments, the second cell culture medium includes an iPSC medium. An iPSC medium may include, for example, ESSENTIAL 8 Medium (Thermo Fisher Scientific, Waltham, MA), ESSENTIAL 6 Medium (Thermo Fisher Scientific, Waltham, MA), or mTeSR1 (StemCell Technologies, Vancouver, Canada). In some embodiments, the second cell culture medium is preferably ESSENTIAL 8 Medium. Surprisingly, although ESSENTIAL 8 Medium was developed to support the growth of induced pluripotent stem cells (iPSCs) without differentiation, it can, as further described herein be used to differentiate iPSCs to an organoid including cartilage and to sustain differentiated cartilage in cell culture.

In some embodiments, the second cell culture medium includes a neural medium. A neural medium may include, for example, DMEM or DMEM F-12, etc., or a combination thereof.

In some embodiments, the cell culture medium does not include a neurotrophin. In some embodiments, the cell culture medium is preferably a chemically defined media, that is, a media that does not include serum or other animal-derived components.

In some embodiments, the second cell culture medium includes a neural induction factor, a neural growth factor, or both. A neural induction factor and/or a neural growth factor may include, for example, N2, B27, fibroblast growth factor (also known as bFGF, FGF2 or FGF-β), transforming growth factor beta (TGFβ), insulin, ascorbate, or glutamate, etc., or a combination thereof.

In some embodiments, the second cell culture medium includes a chondrogenic media. A chondrogenic media promotes formation and maturation of chondrocytes. A chondrogenic media may include, for example, transforming growth factor beta 1 (TGFβ1), transforming growth factor beta 3 (TGFβ3), growth differentiation factor 5 (GDF-5), bone morphogenetic protein 2 (BMP-2), etc., or a combination thereof. In some embodiments, a chondrogenic media includes ESSENTIAL 8 media which includes insulin, selenium, transferrin, L-ascorbic acid, FGF2, and TGFβ (or NODAL) in DMEM/F12 with pH adjusted with $NaHCO_3$. Additional or alternative exemplary chondrogenic media include StemXVivo Chondrogenic Base Media (R&D Systems, Minneapolis, MN); MesenCult-ACF Chondrogenic Differentiation Basal Medium (STEMCELL Technologies, Vancouver, BC); hMSC Chondrogenic Basal Medium (Lonza, Basel, Switzerland); and chondrogenic differentiation medium as described in Solchaga et al., Methods Mol Biol. 2011; 698: 253-278 . . .

In some embodiments, the second cell culture medium includes a growth and differentiation factor that promotes formation and maturation of hyaline cartilage including, for example, transforming growth factor beta 1 (TGFβ1), transforming growth factor beta 3 (TGFβ3), growth differentiation factor 5 (GDF-5), bone morphogenetic protein 2 (BMP-2), etc., or a combination thereof. For example, in some embodiments, the second cell culture medium includes GDF-5 or BMP-2 or both. In some embodiments, the cell culture medium includes a growth and differentiation factor that promotes formation and maturation of bone, an epithelial cell, or fibrous connective tissue.

In some embodiments, the second cell culture medium preferably does not include a media including tumor-derived basement membrane components.

Cell Culture Process in Cell Culture Device

Once transferred to the cell culture device, the cells may be cultured under any suitable conditions. For example, in some embodiments, the cells may be cultured at a temperature in the range of 32° C. to 40° C. In some embodiments, the cells may be cultured at 37° C. In some embodiments, the cells may be cultured at room temperature (for example, a temperature in a range of 20° C. to 25° C.). In some embodiments, the cells may be cultured under hypoxic conditions. Hypoxic conditions, as used herein, refer to an environment having less than 20% oxygen.

The second cell culture medium may be changed as required to maintain cell growth. In some embodiments, the cells may be passaged every 3-4 days.

In some embodiments, the culture process may include periodically detaching the cells and/or organoids from a surface of the flasks. For example, the method may include removing the cell and/or organoid from a gas permeable membrane surface at least once during cell culture.

In some embodiments, including when the cell culture medium includes a cell culture matrix, the cell culture matrix may be removed from the organoids using mechanical methods (for example, with tweezers, a scalpel, and/or forceps) and/or by enzymatic methods. An enzymatic method may include, for example, using one ore more of hyaluronidase, chitosanase, trypsin, DNase, and a collagenase. In some embodiments, the cell culture matrix may be removed using the Cell Retrieval Kit from BRTI Life Sciences (Two Harbors, MN). In some embodiments, the cell culture matrix may disintegrate, making removal unnecessary.

The cells may be cultured in the cell culture device for at least 1 week, at least 2 weeks, at least 3 weeks, at least 4 weeks, 5 weeks, 6 weeks, 7 weeks, at least 8 weeks, at least 9 weeks, at least 10 weeks, at 11 weeks, at least 12 weeks, at least 4 months, at least 5 months, at least 6 months, at least 7 months, at least 8 months, or at least 1 year. In some embodiments, the cells may be cultured for up to 6 months, up to 7 months, up to 8 months, up to 9 months, up to 10 months, up to 11 months, up to 1 year, or up to five years.

In some embodiments, organoids may form after 3 days, after 5 days, after 7 days, after 2 weeks.

In some embodiments, A9 neurons may be present in the organoid after at least 7 days, after at least 2 weeks, after at least 3 weeks, after at least 1 month, after at least 6 weeks, after at least 2 months, or after at least 3 months.

In some embodiments, cartilage (including, for example, hyaline cartilage) may be present in the organoid after 1 week, at least 2 weeks, at least 3 weeks, at least 4 weeks, 5 weeks, 6 weeks, at least 7 weeks, 8 weeks, 9 weeks, or 10 weeks, 11 weeks, or 3 months.

In some embodiments, chondrocyte progenitor or precursor cells may be present after at least 1 week, at least 2 weeks, 3 weeks, 4 weeks, 5 weeks, 6 weeks, 7 weeks, 8 weeks, 9 weeks, or 10 weeks, 11 weeks, or 3 months.

In some embodiments, continued culture of the cells results in loss of the neural elements (for example, neurons, oligodendrocytes, and astrocytes) and in increasing amounts of cartilage, bone, and/or a cytokeratin-expressing epithelial cell.

Cell Dis-Aggregation, Further Selection, and/or Further Culture

In some embodiments, cells of the organoids may be dis-aggregated to produce a population of individualized cells. In some embodiments, the cell of the organoid may be dissociated by chemical and/or mechanical dissociation.

For example, in some embodiments, the cells may be treated with trypsin and/or EDTA. In some embodiments, the cells may be mechanically dissociated using a pipette.

In some embodiments, a chondrocyte may be isolated using a 2-stage chondrocyte isolation, as described in Example 8. In some embodiments, a chondrocyte may be isolated using a 1-stage chondrocyte isolation, as described in Example 8.

In some embodiments, a dis-aggregated organoid-derived cell may be further cultured. In some embodiments, one or more cells or cell types may be selected (for example, by flow sorting) from the dis-aggregated organoid-derived cells before further culturing.

For example, as described in Example 2, dis-aggregated cells may be plated on MATRIGEL-coated coverslips. In some embodiments, dis-aggregated cells may be cultured on an ultra-low attachment surface. In some embodiments, ultra-low attachment surface may include a Corning Ultra-Low Attachment Surface.

In some embodiments, a dis-aggregated organoid-derived cell may be re-embedded in a hydrogel for further culture. Such culture may be particularly useful for culturing cells for tissue engineering or repair purposes.

In some embodiments, a dis-aggregated cell may be cultured in Neurobasal Medium (Thermo Fisher Scientific, Waltham, MA). In some embodiments, the Neurobasal Medium may include a B-27 supplement (Thermo Fisher Scientific, Waltham, MA).

Additionally or alternatively, a dis-aggregated cell may be cultured in a cell culture medium that includes a growth and differentiation factor that promotes formation and maturation of hyaline cartilage and/or a chondrocyte. Such media may include a chondrogenic media. Such growth and differentiation factors may include chondrogenic factors. Exemplary growth and differentiation factors include, for example, TGFβ1, TGFβ3, GDF-5, FGF2, BMP-2, BMP-9, GDF5, etc. In an exemplary embodiment, the cell culture medium includes ESSENTIAL 8 media which includes insulin, selenium, transferrin, L-ascorbic acid, FGF2, and TGFβ (or NODAL) in DMEM/F12 with pH adjusted with NaHCO$_3$.

For example, as described in Example 8, dis-aggregated cells may be cultured in a ESSENTIAL 8 media on an ultra-low attachment surface. As further described in Example 8, chondrocytes may be isolated from the organoid and/or the disaggregated cells prior to being cultured on the ultra-low attachment surface. Further culture of an isolated chondrocyte in a chondrogenic media including, in some embodiments, on an ultra-low attachment surface, may be used to form a chondrocyte aggregate. As further described in Example 8, placing chondrocytes isolated from multi-tissue organoids into ultra-low attachment plates and culturing them at 37° C. in 5% CO$_2$ in ESSENTIAL 8 medium or other chondrogenic media generates chondrocyte aggregates.

Additionally or alternatively, a dis-aggregated cell may be cultured in a cell culture medium that includes a growth and differentiation factor that promotes formation and maturation of bone. Such growth and differentiation factors may include, for example, bone morphogenetic proteins (for example, BMP-2, BMP-7), vascular endothelial growth factor (VEGF), osteogenic medium (OM) as described in Tirkkonen et al. 2013 *Eur. Cells Mat.* 25:144-158, etc.

Additionally or alternatively, a dis-aggregated cell may be cultured in a cell culture medium that includes a growth and differentiation factor that promotes formation and maturation of an epithelial cell including, for example, a cytokeratin-expressing epithelial cell. Such growth and differentiation factors may include, for example insulin, transferrin, epidermal growth factor (EGF), hydrocortisone, T3, cholera toxin (CT), and bovine hypothalamus extract (BHE), etc.

Additionally or alternatively, a dis-aggregated cell may be cultured in a cell culture medium that includes a growth and differentiation factor that promotes formation and maturation of fibrous connective tissue.

Features of the Organoid

The methods described herein may be used to produce a multi-tissue organoid (MTO). In some embodiments, the MTO preferably include cartilage. In some embodiments, the MTO may include a midbrain organoid that includes an A9 neuron and/or an A10 neuron. In some embodiments, the MTO includes a brain organoid. In some embodiments, the MTO includes a neuroectodermal organoid. As used herein, a neuroectodermal organoid refers to an organoid that includes brain tissues including, for example A9 neurons, and tissues that arise from the embryonic neural tube and neural crest including, for example, cartilage, bone, an osteocyte, a mesenchymal stem cell, a skeletal stem cell, a cytokeratin-expressing epithelial cell, and/or fibrous connective tissue.

In some embodiments, the MTO includes one or more of an oligodendrocyte, an astrocyte, a polydendrocyte, a neural precursor cell, a neural stem cell, a neural progenitor cell, a neural crest cell, a chondrocyte, a cytokeratin-expressing epithelial cell, a type 1-collagen-expressing cell, an osteocyte, a mesenchymal stem cell, a skeletal stem cell, a derivative of an oligodendrocyte, a derivative of an astrocyte, a derivative of a polydendrocyte, a derivative of a neural precursor cell, a derivative of a neural stem cell, a derivative of a neural progenitor cell, a derivative of a neural crest cell, a derivative of a chondrocyte, a derivative of a cytokeratin-expressing epithelial cell, a derivative of a type 1-collagen-expressing cell, a derivative of an osteocyte, a derivative of a mesenchymal stem cell, or a derivative of a skeletal stem cell, or a mixture thereof.

Surprisingly, the methods described herein-which were developed for producing brain organoids—can also be used to create an MTO that includes cartilage. Previous attempts to create cartilage typically included using feeder cells or undefined components (for example, MATRIGEL). (See, for example, Lietman, World J Orthop. 2016 Mar. 18; 7(3):149-155.) In contrast organoids prepared by the methods described herein can be produced without the use of feeder cells—which are problematic to the resulting tissue due to contamination issues—an embryoid body stage—which is problematic because of resulting heterogeneity—or undefined components—which are problematic to the resulting tissue due to resulting variabilities. In addition, organoids including chondrocytes prepared by the methods described herein are achieved using much lower levels of TGFβ than has previously been used to derive chondrocytes from mesenchymal stem cells or iPSCs.

In some embodiments, an oligodendrocyte may be identified by its expression of myelin basic protein (MBP). In some embodiments, an astrocyte may be identified by its expression of glial fibrillary acidic protein (GFAP). In some embodiments, a polydendrocyte may be identified by its expression of chondroitin sulfate proteoglycan 4 (CSPG4). In some embodiments, a neural stem cell and/or a neural progenitor cell may be identified by its expression of Sox1, Sox2, and/or Nestin. In some embodiments, a neural crest cell may be identified by its expression of FoxD3. In some embodiments, a chondrocyte may be identified by its expression of type 2 collagen (T2Col) and/or aggrecan. In some embodiments, a chondrocyte may be detected by the protein or gene expression of a marker including, for example, CD9, CD10, CD14, CD26, CD44, CD49a, CD49b, CD49c, CD49e, CD49f, CD51, CD54, CD56 CD58, CD63, CD71, CD81, CD82, CD90, CD95, CD99, CD105, CD106, CD119, CD120a, CD130, CD140a, CD151, CD166, CD221, aggrecan, type II collagen (also referred to as type 2 collagen), type VI collagen, type IX collagen, type X collagen, type XI collagen, annexin A6, SRY-Box 9 (Sox9), matrilin 1, hyaluronan synthase, integral membrane protein 2a, chondroadherin, link protein 1, cathepsin B, cartilage acidic protein 1, or epiphycan, or a combination thereof.

In some embodiments, the organoid includes a cell expressing GFAP; a cell expressing microtubule associated protein 2 (MAP2); a cell expressing MBP; a cell expressing type 1 collagen (T1Col); a cell expressing type 2 collagen (T2Col); a cell expressing aggrecan; or a cell expressing cytokeratins, or a combination thereof (including organoids that include multiple type of cells and organoids that include cells expressing more than one of GFAP, MAP2, MBP, T1Col, T2Col, aggrecan, and cytokeratins).

In some embodiments, a cell of the organoid may exhibit typical neuronal electrophysiology. Neuronal electrophysiology may be measured by any suitable method including, for example, by patch clamp analysis.

In some embodiments, the presence of an A9 neuron is characterized by expression of at least one of tyrosine hydroxylase, Girk2, and Nurr1. For example, in some embodiments, the presence of an A9 neuron is characterized by expression of tyrosine hydroxylase and Girk2.

In some embodiments, the presence of an A10 neuron is characterized by the expression of at least one of tyrosine hydroxylase, calbindin 1 (CALB1), and Nurr1. For example, in some embodiments, the presence of an A10 neuron is characterized by expression of tyrosine hydroxylase and CALB1.

In some embodiments, the organoid includes a cell exhibiting expression of at least one of nucleostemin (GNL3), SOX1, SOX2, β-3 tubulin (TUBB3), and nestin (NES). In some embodiments, expression of at least one of GNL3, SOX1, SOX2, TUBB3, and NES may indicate the presence of a neural stem/progenitor cell.

In some embodiments, the organoid includes a cell exhibiting expression of at least one of nuclear receptor subfamily 4 group A member 2 (NR4A2); LIM homeobox transcription factor 1 alpha (LMX1A); forkhead Box A2 (FOXA2); and orthodenticle homeobox 2 (OTX2). In some embodiments, expression of at least one of NR4A2, LMX1A, FOXA2, and OTX2 may indicate the presence of a dopaminergic neuron progenitor.

In some embodiments, the organoid includes a cell exhibiting expression of at least one of tyrosine hydroxylase (TH); torsin family 1 member A (TORIA); corin, serine peptidase (CORIN); and dopa decarboxylase (DDC). In some embodiments, expression of at least one of TH, TORIA, (CORIN, and DDC may indicate the presence of a dopaminergic neuron.

In some embodiments, the organoid includes a cell exhibiting expression of potassium voltage-gated channel subfamily J member 6 (KCNJ6). In some embodiments, expression of KCNJ6 may indicate the presence of an A9 neuron.

In some embodiments, the organoid includes a cell exhibiting expression of calbindin 1 (CALB1). In some embodiments, expression of CALB1 may indicate the presence of an A10 dopaminergic neuron.

In some embodiments, the expression of a marker that indicates a cell type may be measured by detecting protein expression and/or by detecting gene expression. Protein expression and/or gene expression may be detected using any suitable method or combination of methods. For example, expression may be detected by a technique including, for example, immunohistochemical (IHC) staining, immunofluorescence, quantitative Western blot, flow cytometry, RNA-Seq gene expression analysis, quantitative RT-PCR, mass spectroscopy, microarray analysis, etc. In some embodiments, methods of detecting protein expression may be preferred for determining whether a protein is present in a cell because it is possible for an RNA to be expressed but not transcribed into a protein.

Uses for the Cells, Tissue, Matrix, and/or Organoids

In another aspect, this disclosure describes using an organoid, made as described herein; a tissue (for example, hyaline cartilage) of the organoid; a cell of the organoid, a matrix of the organoid, a chondrocyte derived from the organoid, and/or a chondrocyte aggregate derived from the organoid for an experimental or therapeutic use.

Therapeutic uses may include the repair of cartilaginous structures including, for example, an intervertebral disk, a nasal septum, nasal cartilage, meniscus structures of joints, tracheal-bronchial cartilage, etc.

For example, in some embodiments, the hyaline cartilage or a chondrocyte aggregate may be used for the repair of articular cartilage due to traumatic injury, osteoarthritis, etc.

In some embodiments, the hyaline cartilage, a chondrocyte, and/or a chondrocyte aggregate derived from the organoid may be used in reconstructive surgery (including, for example, for ear or nose repair), for repair or replacement of tracheal and bronchial cartilage, and for repair or replacement of intervertebral discs.

In some embodiments, a cell (including, for example, a chondrocyte) derived from the organoid may be used in a bio-printing application.

In some embodiments, the hyaline cartilage and/or a chondrocyte derived from the organoid may be used for in vitro modeling of a cartilage disorder.

The present invention is illustrated by the following examples. It is to be understood that the particular examples, materials, amounts, and procedures are to be interpreted broadly in accordance with the scope and spirit of the invention as set forth herein.

EXAMPLES

Example 1

Materials

Passaging Solution/Citrate Buffer (Solution of 0.3 M Potassium Chloride and 0.015 M Sodium Citrate-dihydrate)

The iPSC lines used are described in Table 1.

TABLE 1

| iPS Line | Cell Line | Sex | Derived cell type | Delivery Method | Reprogramming Factors |
|---|---|---|---|---|---|
| R58 | ALD1 | M | keratinocytes | Retrovirus | OCT4, SOX2, KLF4, c-MYC (Addgene) |
| R76 | ALD2 | M | fibroblasts | Retrovirus | OCT4, SOX2, KLF4, c-MYC (Addgene) |
| R77 | ALD3 | M | keratinocytes | Cytotune 2.0 | polycistronic Klf4-Oct3/4-Sox2, cMyc, and Klf4. |
| CS1 | WT1 | F | fibroblasts | Retroviral | OCT4, SOX2, KLF4, c-MYC (Addgene) |
| CEC | WT2 | M | corneal epithelial | Cytotune 1.0 | Oct3/4, Sox2, Klf4, and cMyc |
| D12-9 | WT3 | F | peripheral blood | Cytotune 1.0 | Oct3/4, Sox2, Klf4, and cMyc |
| GRIPS | WT4 | M | foreskin fibroblasts | Cytotune 1.0 | Oct3/4, Sox2, Klf4, and cMyc |
| CBB | — | F | cord blood | Retroviral | OCT4, SOX2, KLF4, c-MYC |
| 1024 | — | M | bone marrow | Sendai virus | OCT4, SOX2, KLF4, c-MYC |

Methods

Cell Culture with Cell-Mate 3D

1. Add 50 mL ESSENTIAL 8 media (Catalog No. A151700, Thermo Fisher Scientific, Waltham, MA) to GREX 100 cell culture device (Catalog No. 800500S, Wilson Wolf Corporation, St. Paul, MN) and set aside.
2. Wash 3 T-175 flasks containing iPSCs one time with PBS (17.5 mL each).
3. Add 17.5 mL Passaging Solution/Citrate Buffer into each flask. Wait and observe for 5 minutes or until cells begin to lift off.
4. Aspirate off Passaging Solution/Citrate buffer.
5. Wash cells off of each T-175 flask with 10 mL DMEM/F12 (Thermo Fisher Scientific, Waltham, MA) and collect cells into a 50 mL conical tube. Total volume comes to 30 mL.
6. Optionally, rinse all flasks with additional 10 mL DMEM/F12. (Total volume is 40 mL.)
7. Spin in centrifuge for 5 minutes at 150 g/1200 RPM.
8. Aspirate supernatant and resuspend cell pellet in 250 µL of Cell-Mate3D hydration fluid (Catalog No. CM-1001, BRTI Life Sciences, Two Harbors, MN).
9. Add hydration fluid mixture to dry blend while vortexing, according to manufacturer's protocol.
10. Transfer Cell-Mate3D to funnel apparatus, according to manufacturer's protocol.
11. Centrifuge to 2700 rpm and stop, according to manufacturer's protocol.
12. Use scalpel to slice small pieces (10 µL to 30 µL) of Cell-Mate and add to prepared Wilson Wolf flask.
13. Culture cells in a 37° C. incubator (5% $CO_2$, 20% $O_2$); change media every 3-4 days.

Histology and Immunohistochemistry and Immunocytochemistry

Histology and Immunohistochemistry and Immunocytochemistry were performed as described in Lindborg et al. Stem Cells Translational Medicine, 2016, 5(7):970-979.

Gene expression analysis and bioinformatics

Organoids including 3 biological replicates from each of 2 different input iPS cell lines were collected at week 6 and lysed in RLT buffer (Qiagen, Venlo, The Netherlands) and stored at −80° C. until processed. RNA was isolated from cell lysates using the RNA mini plus kit (Qiagen) according to manufacturer's instructions. RNAseq (HiSeq, Illumina, San Diego, CA) gene expression analysis was performed at University of Minnesota Genomics Center. An established analysis pipeline developed and maintained by the University of Minnesota Informatics Institute (UMII) was used to analyze the raw sequence data. The detailed methods are available on the world wide web at bitbucket.org/jgarbe/gopher-pipelines/wiki/Home. Briefly, the pipeline first performs quality control and adapter trimming using FastQC and Trimmomatic, respectively, and then uses HISAT2 for reads alignment. Finally, the transcript abundance was estimated using Cufflinks and SubRead.

Results

Figure 1B:
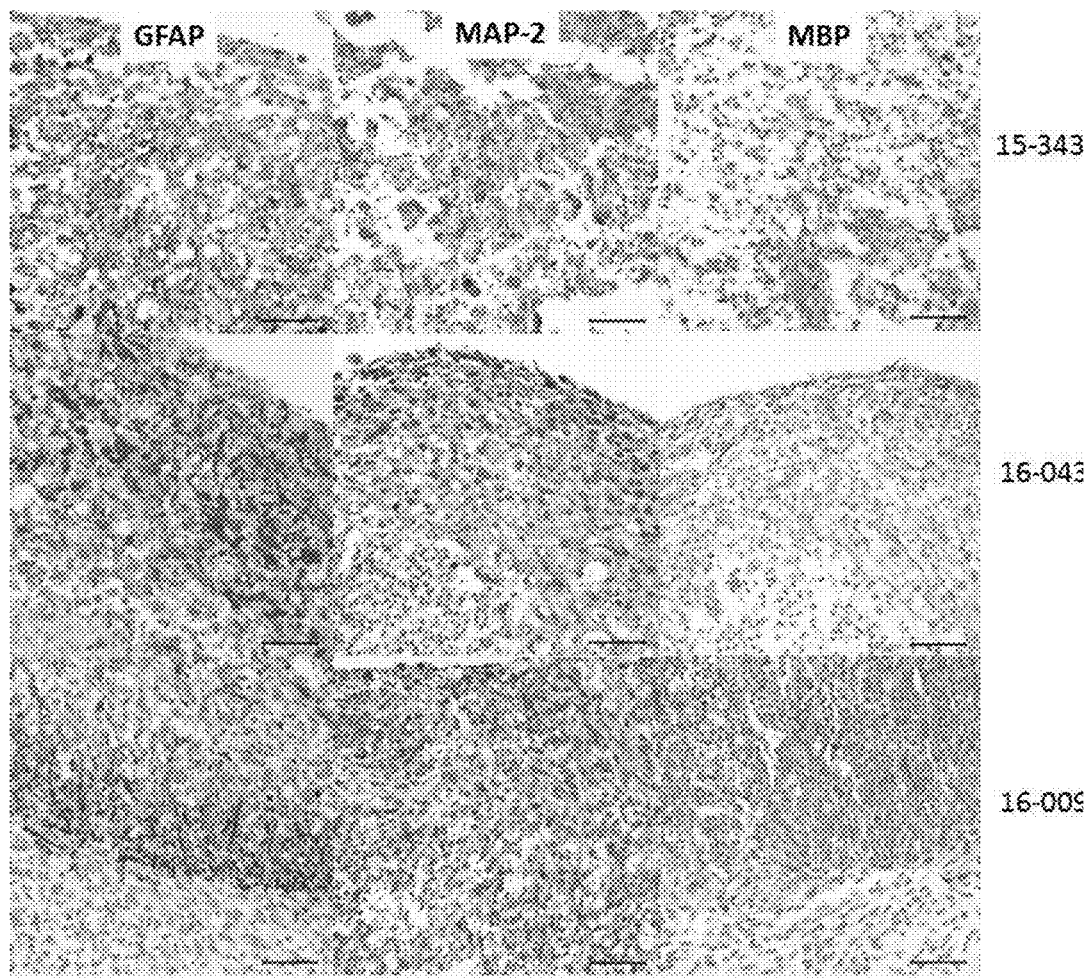
Figure 2:
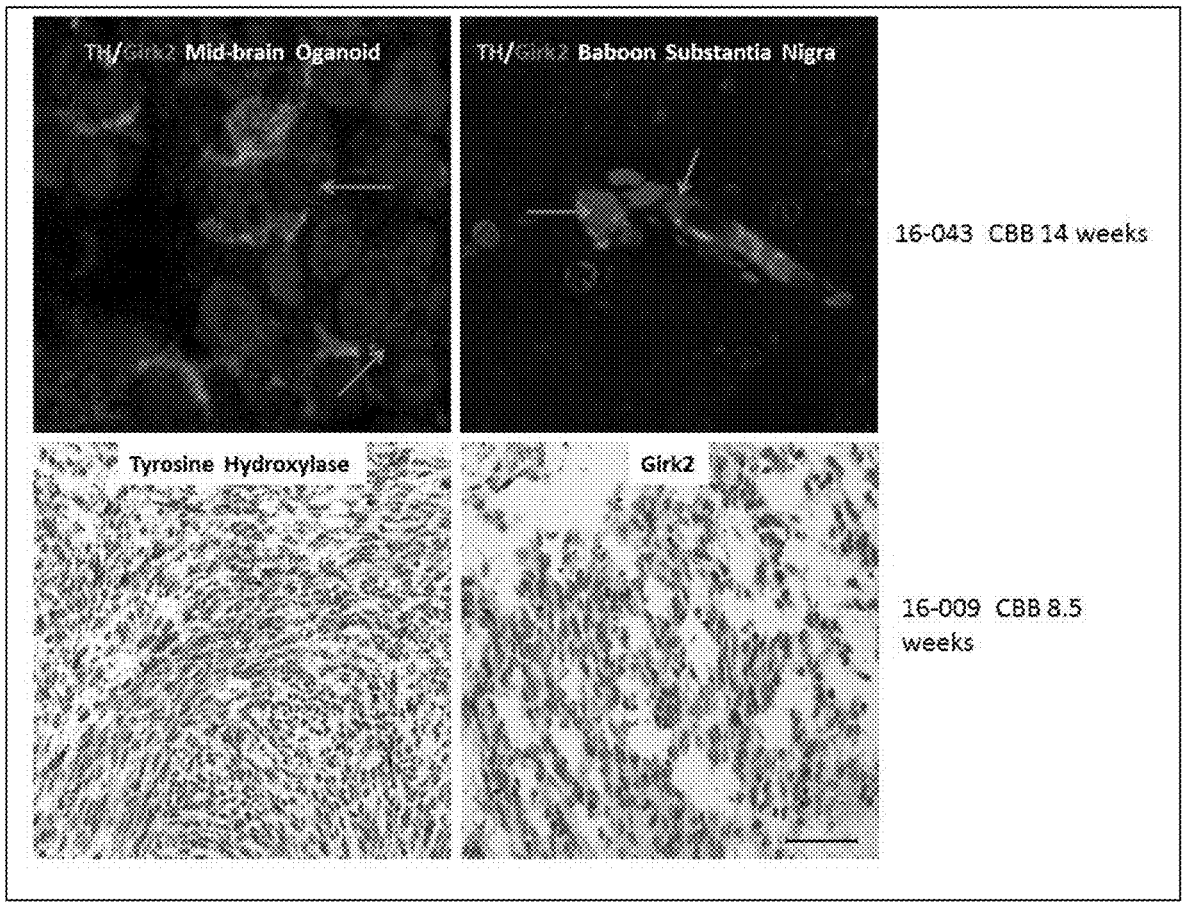
FIG. 2 shows exemplary histology of multi-tissue organoids exhibiting features of a midbrain organoid. Upper panels: Left image shows confocal microscopy of histologic sections of an organoid derived from iPSC cell line CBB. Cells were cultured for 14 weeks in ESSENTIAL 8 media in a GREX 100 cell culture device. Immunofluorescent double labeling for tyrosine hydroxylase (TH) and G Protein-Activated Inward Rectifier Potassium Channel 2 (Girk2) shows their co-localization (arrows), confirming the presence of A9 type nigral dopaminergic neurons in the organoid. Right image shows control staining for TH and Girk2 double labeling in neurons in the substantia nigra of a normal baboon brain. Lower Panels: Immunohistochemical labeling of adjacent histologic sections of a brain organoid (derived from the CBB cell line and cultured for 8.5 weeks) showing tyrosine hydroxylase (left) and Girk2 labeling (right) in neurons, consistent with A9 dopaminergic neurons.
Figure 3:
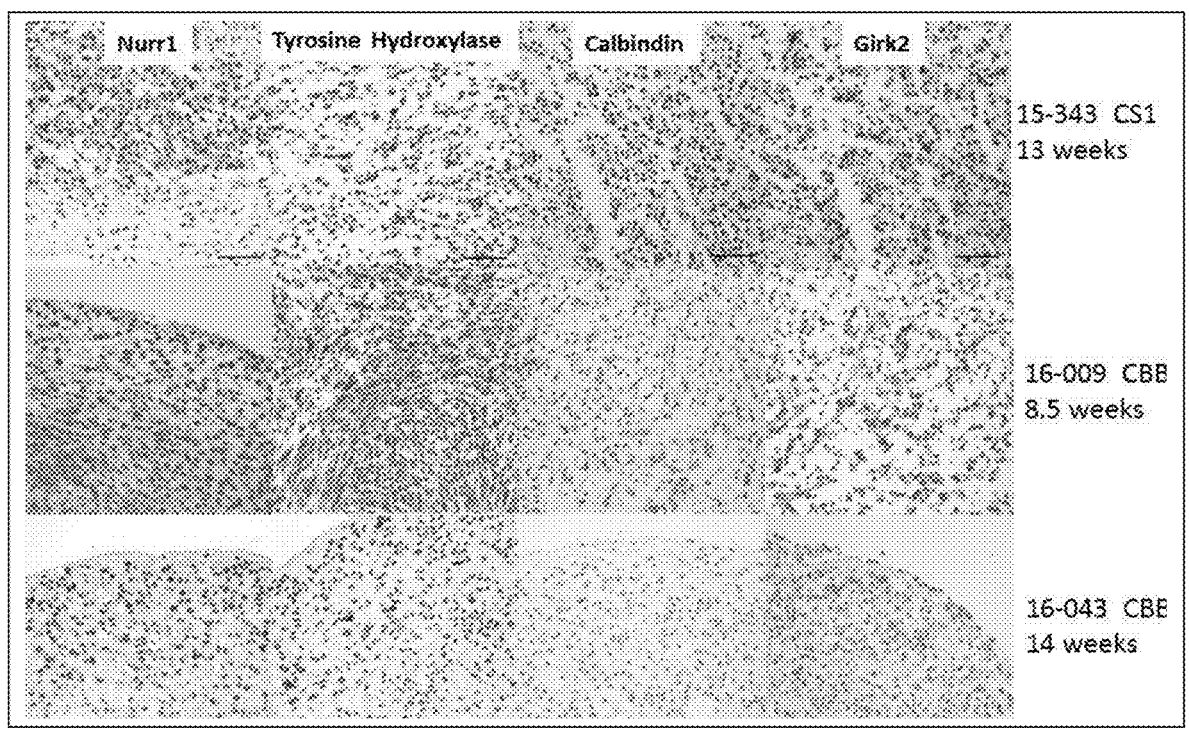
FIG. 3 shows immunohistochemical staining of organoids derived from cell lines CS1 (13 weeks in GREX 100 cell culture device) and CBB (8.5 weeks & 14 weeks in GREX 100 cell culture device). In all three conditions, positive nuclear staining was seen for Nurr1, a marker of dopaminergic neuron precursors, and cytoplasmic labeling was present for tyrosine hydroxylase and Girk2, markers of A9 nigral dopaminergic neurons. None of the conditions showed positive staining for calbindin which is a marker of A10 dopaminergic neurons.

Histologic analysis of organoids between 8.5 weeks and 14 weeks in culture showed extensive regions of neural tissue development in the organoids. Immunohistochemical stains in this time frame showed evidence of development of characteristic brain cell lineages including mature neurons (MAP2), oligodendrocytes (MBP), and astrocytes (GFAP) (FIG. 1). At these time points, there was also consistent IHC evidence characteristic of midbrain dopaminergic neurons with IHC labeling for tyrosine hydroxylase, Girk2, and Nurr1 (FIGS. 2 & 3). Furthermore, specification of A9 nigral dopaminergic neurons was confirmed by the presence of tyrosine hydroxylase (TH)/Girk2 double immunofluorescent positive neurons (FIG. 2).

Figure 4:
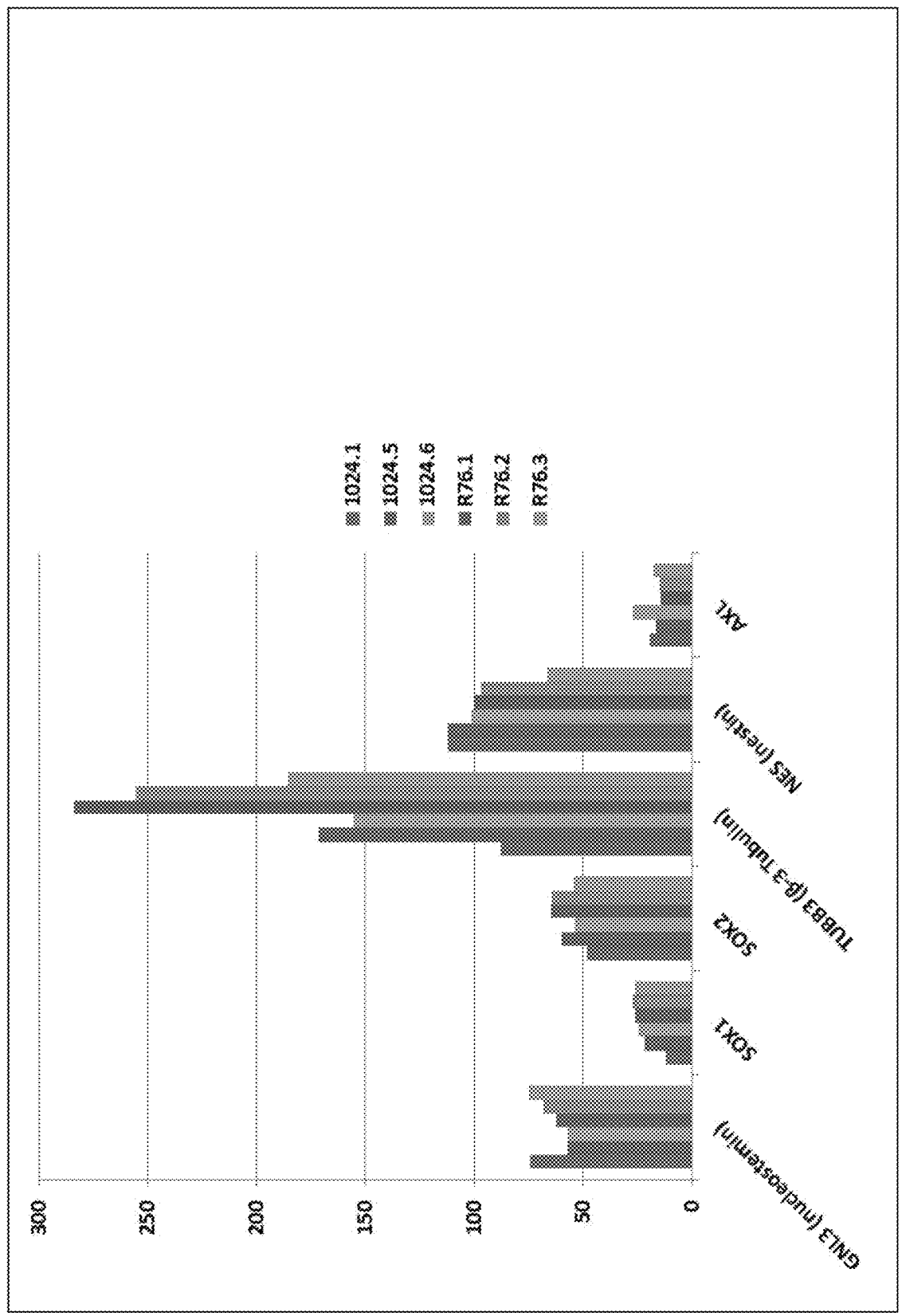
FIG. 4 shows expression of neural stem/progenitor cell markers in exemplary organoids. RNA-Seq gene expression analysis of pooled, 5-6 week organoids derived from 2 different iPSC lines (1024 & R76) with 3 biological replicates of each. The panel shows moderate to high expression of genes that are markers of neural stem/progenitor cells (GNL3, nucleostemin; SOX1; SOX2; TUBB3, β-3 tubulin; and NES, nestin)) and shows a consistent pattern of expression of these genes among the replicates. AXL codes for the receptor protein for the Zika virus.
Figure 5:
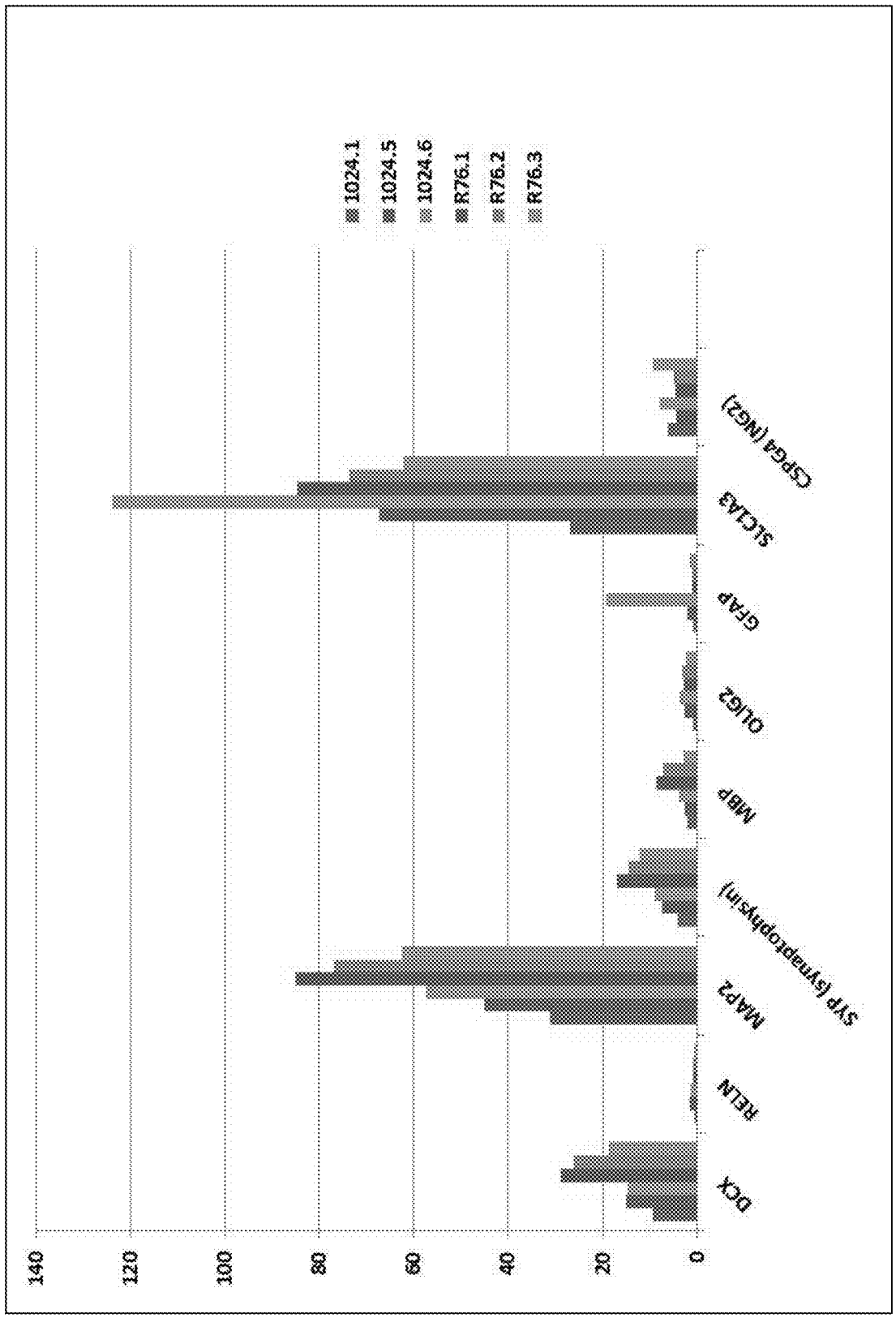
FIG. 5 shows expression of brain cell-type markers in exemplary organoids. RNA-Seq gene expression analysis of pooled, 5-6 week organoids derived from 2 different iPSC lines (1024 & R76) with 3 biological replicates of each. The panel provides evidence for the presence of neurons (indicated by the expression levels of DCX, doublecortin; RELN, reelin; MAP2, microtubule associated protein 2; and SYP, synaptophysin), oligodendrocytes (indicated by the expression levels of MBP, myelin basic protein; OLIG2, oligodendrocyte lineage transcription factor 2), astrocytes (indicated by the expression levels of GFAP, glial fibrillar acidic protein; SLC1A3, solute carrier family 1 member 3), and polydendrocytes (indicated by the expression levels of CSPG4, chondroitin sulfate proteoglycan 4). This mixture of cell types mirrors the patterns of cell populations in normal human brain.
Figure 6:
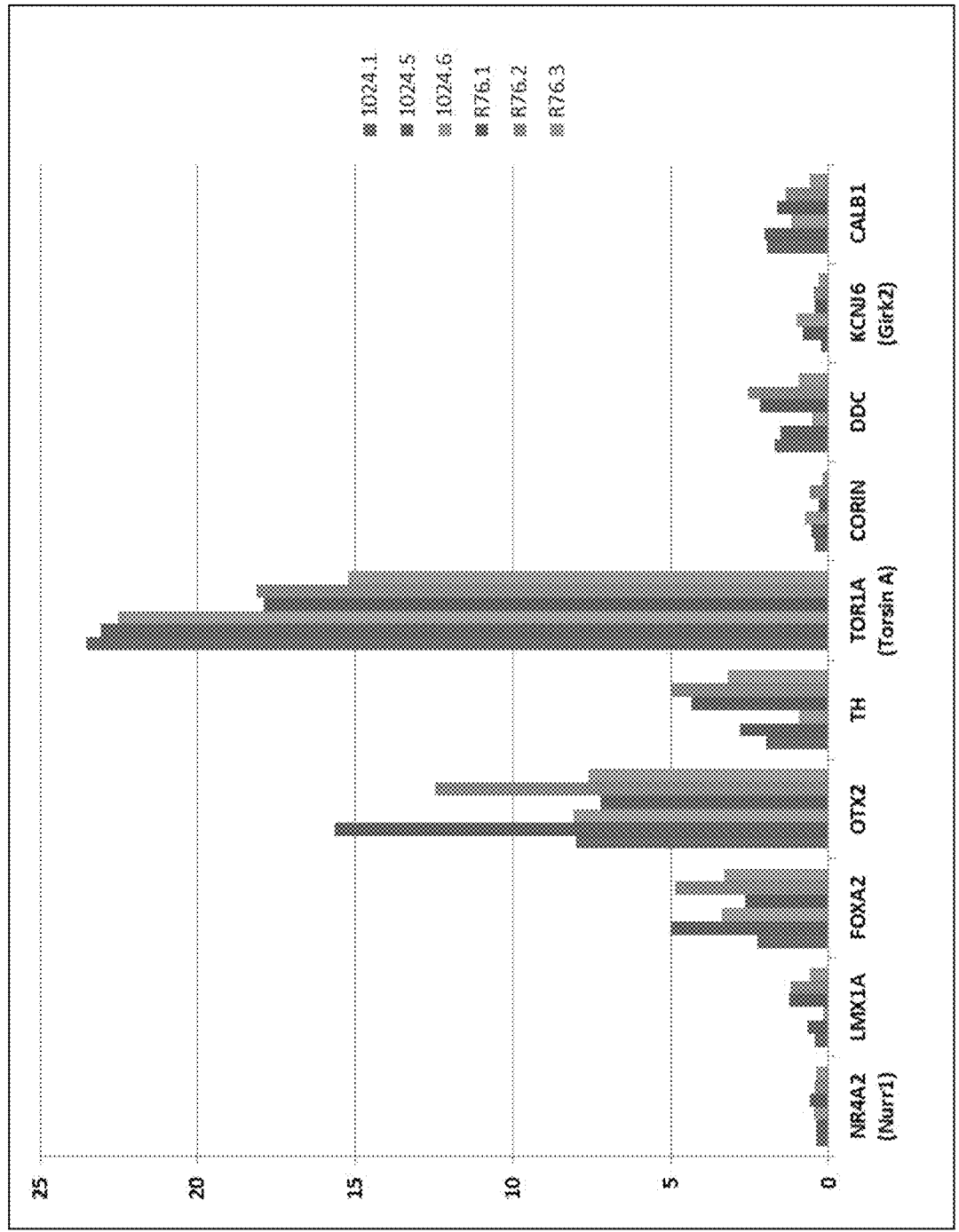
FIG. 6 shows expression of dopaminergic neuron markers in exemplary organoids. RNA-Seq gene expression analysis of pooled, 5-6 week organoids derived from 2 different iPSC lines (1024 & R76) with 3 biological replicates of each. The panel provides evidence for the presence of dopaminergic neuron progenitors (indicated by the expression levels of NR4A2, nuclear receptor subfamily 4 group A member 2; LMX1A, LIM homeobox transcription factor 1 alpha; FOXA2, forkhead Box A2; and OTX2, orthodenticle homeobox 2), dopaminergic neurons (indicated by the expression levels of TH, tyrosine hydroxylase; TOR1A, torsin family 1 member A; CORIN, corin, serine peptidase; and DDC, dopa decarboxylase), A9 nigral dopaminergic neurons (indicated by the expression levels of KCNJ6, potassium voltage-gated channel subfamily J member 6), and A10 dopaminergic neurons (indicated by the expression levels of CALB1, calbindin 1).
Figure 7:
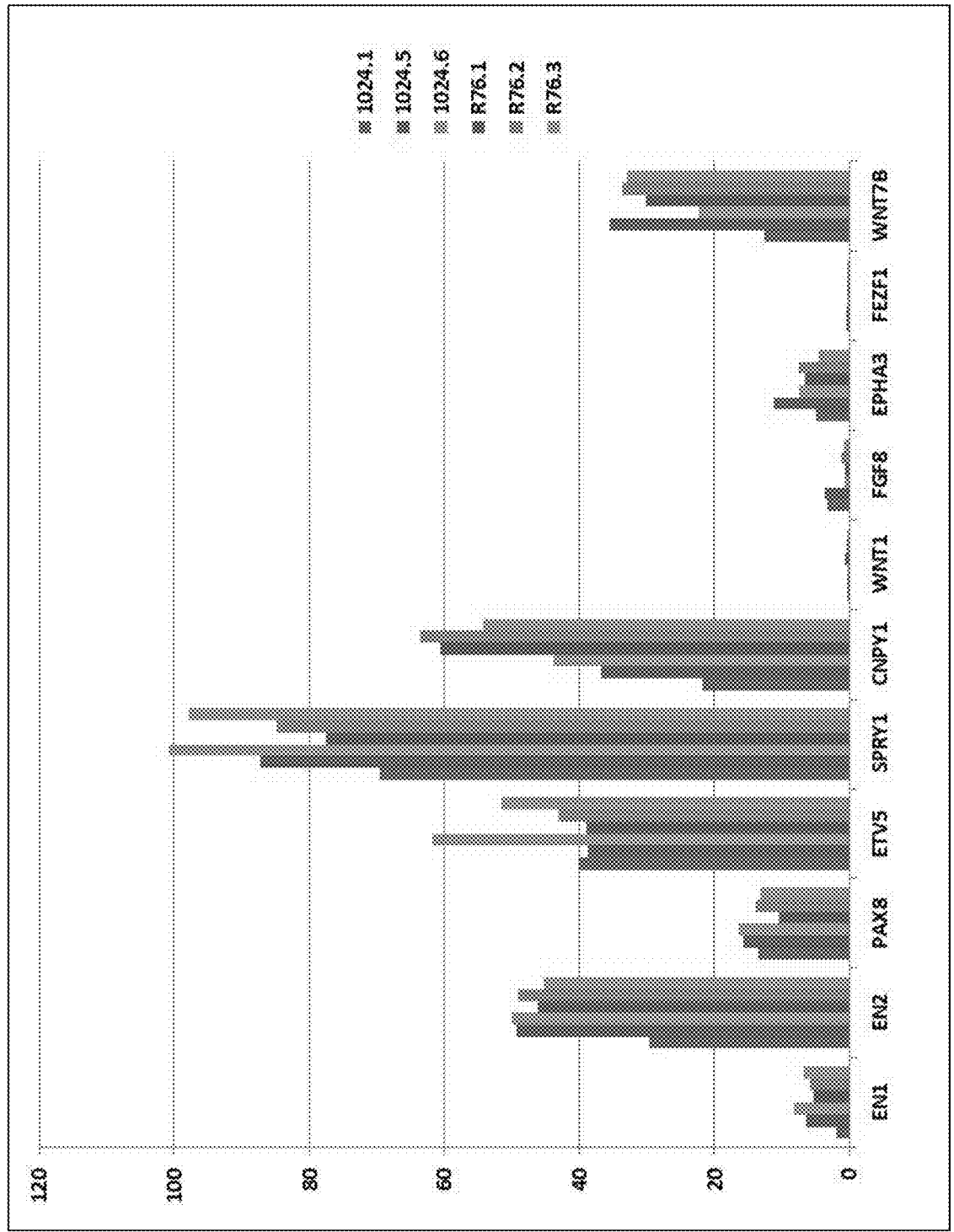
FIG. 7 shows expression of transplant engraftment success markers in exemplary organoids. RNA-Seq gene expression analysis of pooled, 5-6 week organoids derived from two different iPSC lines (1024 & R76) with three biological replicates of each. The panel provides evidence for the presence of moderate to high levels of gene markers associated with positive engraftment outcomes in a rodent model of Parkinson's disease (PD) (EN1, engrailed homeobox 1; EN2, engrailed homeobox 2; PAX8, paired box 8; ETV5, ETS variant 5; SPRY1, Sprouty RTK signaling antagonist 1; CNPY1, canopy FGF signaling regulator 1; WNT1, Wnt family member 1; and FGF8, fibroblast growth factor 8) and very low to moderate levels of expression of genes associated with negative engraftment outcomes in a rodent model of PD (EPHA3, EPH receptor A3; FEZF1, FEZ family zinc finger 1; and WNT7B, Wnt family member 7B).
Figure 8:
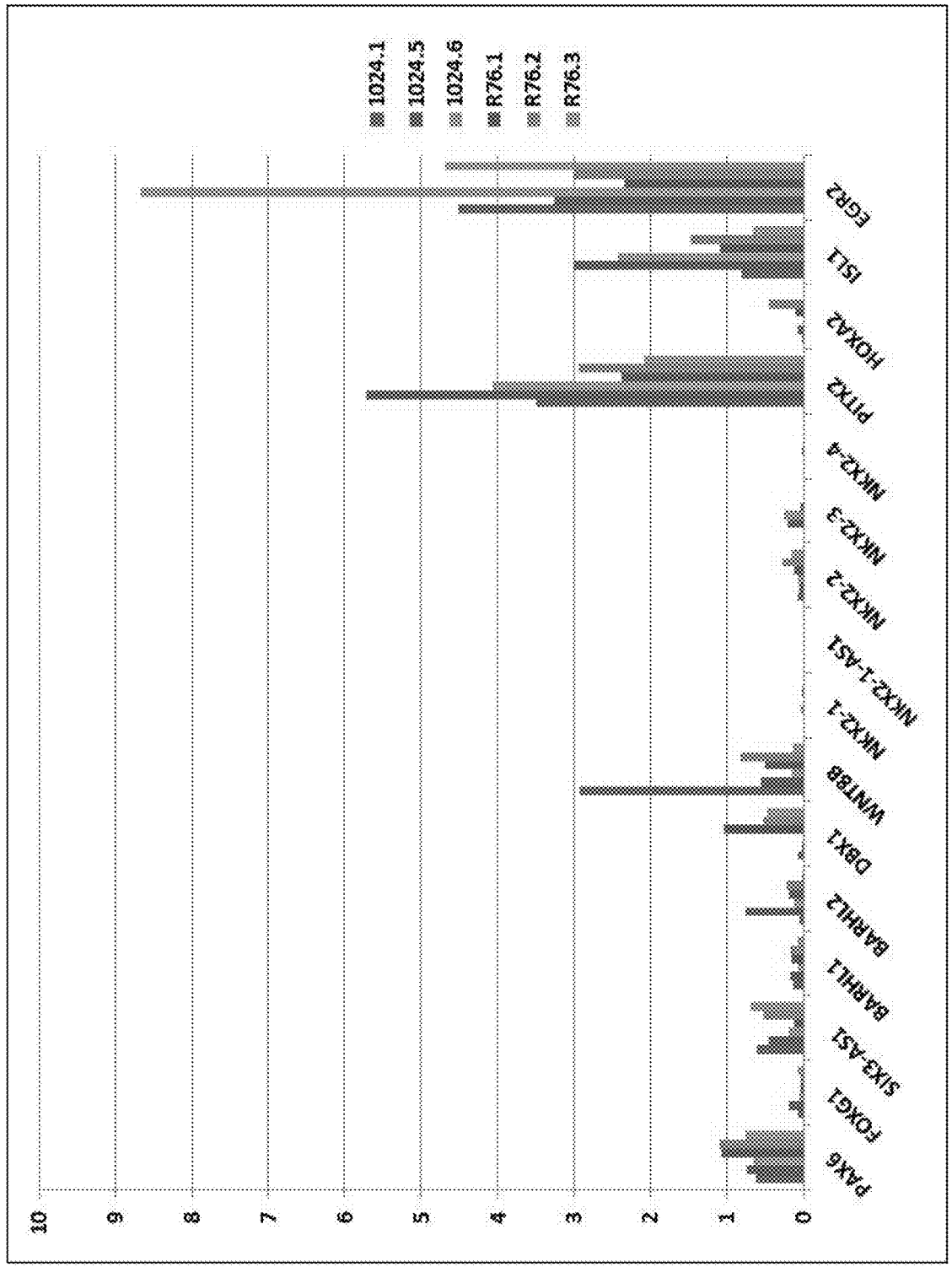
FIG. 8 shows expression of brain regional markers in exemplary organoids. RNA-Seq gene expression analysis of pooled, 5-6 week organoids derived from 2 different iPSC lines (1024 & R76) with 3 biological replicates of each. The panel provides evidence for very low levels of gene markers associated with forebrain development (PAX6, paired box 6; FOXG1, forkhead box G1; SIX3, SIX homeobox 3), very low levels of rostral diencephalic markers (BARHL1, BarH like homeobox 1; and BARHL2, BarH like homeobox 2), very low levels of markers for rostral midbrain (DBX1, developing brain homeobox 1; WNT8B, Wnt family member 8B; NKX2-1 NK2 homeobox 1; NKX2-1-AS1, NKX2-1 antisense RNA 1; NKX2-2, NK2 homeobox 2; NKX2-3, NK2 homeobox 3; NKX2-4, NK2 homeobox 4; and PITX2, paired like homeodomain 2), and low to moderate levels of markers for hindbrain (HOXA2, homeobox A2; ISL1, ISL LIM homeobox 1, and EGR2, early growth response 2).
Figure 9:
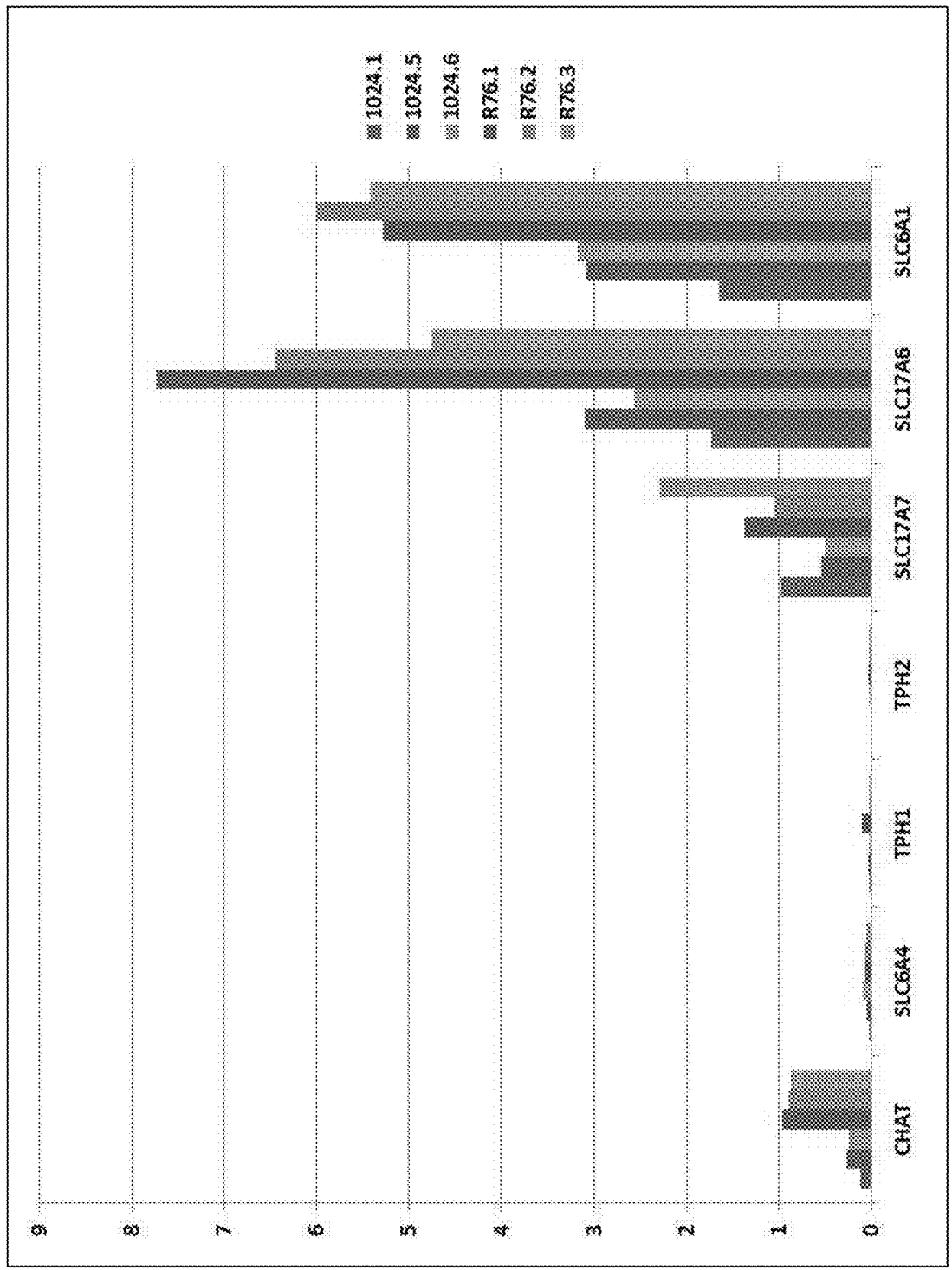
FIG. 9 shows expression of markers for non-dopaminergic neuron types in exemplary organoids. RNA-Seq gene expression analysis of pooled, 5-6 week organoids derived from 2 different iPSC lines (1024 & R76) with 3 biological replicates of each. The panel provides evidence for the presence of low levels of a marker for cholinergic neurons (CHAT, choline o-acetyltransferase), very low to absent levels of markers for serotonergic neurons (SLC6A4, solute carrier family 6 member 4; TPH1, tryptophan hydroxylase 1; and TPH2, tryptophan hydroxylase 2), low to moderate levels of markers for glutaminergic neurons (SLC17A7, solute carrier family 17 member 7; and SLC17A6, solute carrier family 17 member 6) and moderate levels of a GABAergic neuron marker (SLC6A1, solute carrier family 6 member 1).
Figure 10:
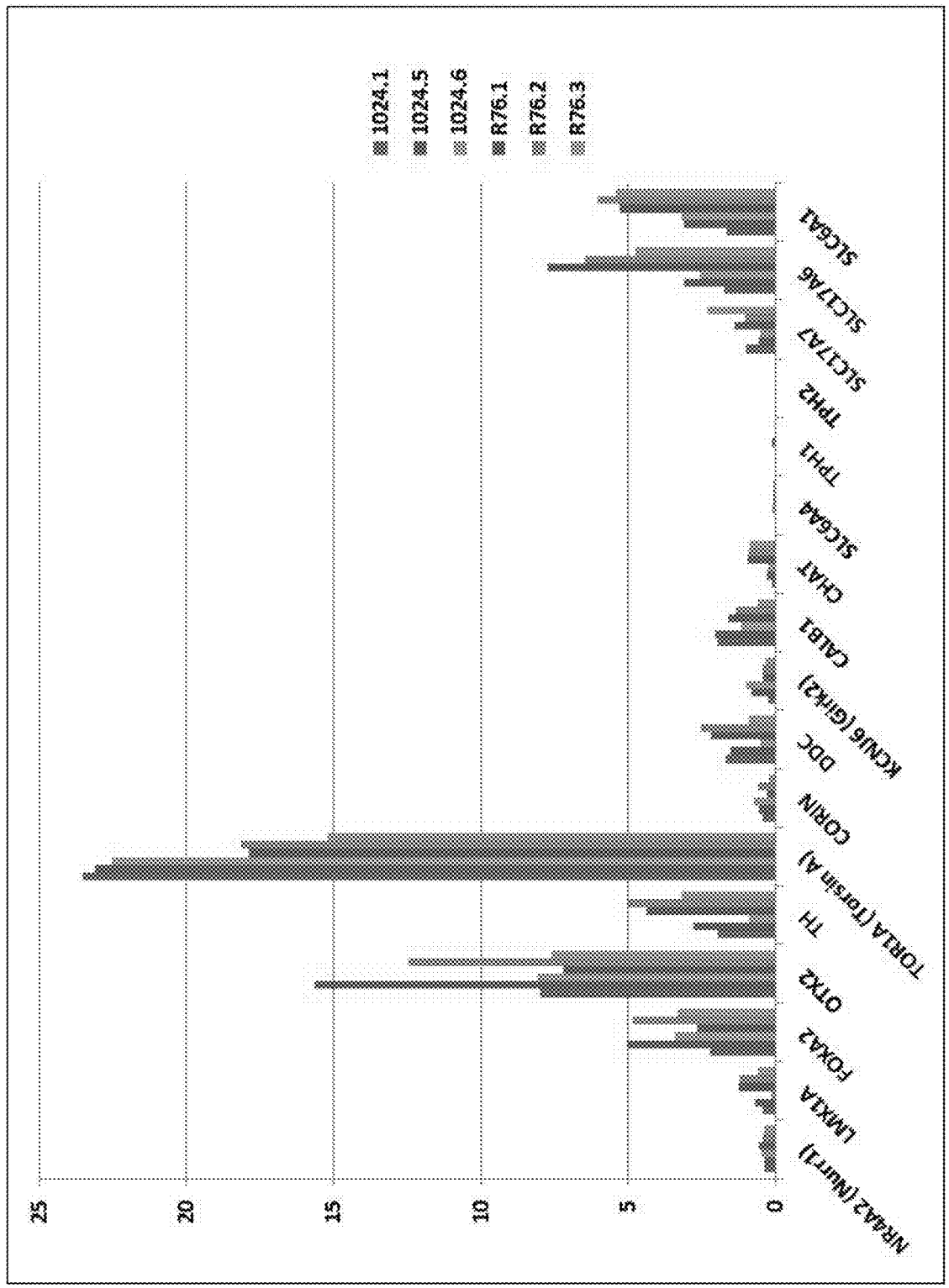
FIG. 10 shows expression of markers of neuron subtypes in exemplary organoids. RNA-Seq gene expression analysis of pooled, 5-6 week organoids derived from two different iPSC lines (1024 & R76) with three biological replicates of each. The panel provides evidence for the preponderance of dopaminergic neuron markers versus other neuronal subtypes in organoids, consistent with a midbrain phenotype. Specifically, there is expression of dopaminergic neuron progenitors (NR4A2, nuclear receptor subfamily 4 group A member 2; LMXIA, LIM homeobox transcription factor 1 alpha; FOXA2, forkhead Box A2; and OTX2, orthodenticle homeobox 2), dopaminergic neurons (TH, tyrosine hydroxylase; TOR1A, torsin family 1 member A; CORIN, corin, serine peptidase; and DDC, dopa decarboxylase), A9 nigral dopaminergic neurons (KCNJ6, potassium voltage-gated channel subfamily J member 6), and A10 dopaminergic neurons (CALB1, calbindin 1). There is also evidence for the presence of low levels of a marker for cholinergic neurons (CHAT, choline o-acetyltransferase), very low to absent levels of markers for serotonergic neurons (SLC6A4, solute carrier family 6 member 4; TPH1, tryptophan hydroxylase 1; and TPH2, tryptophan hydroxylase 2), low to moderate levels of markers for glutaminergic neurons (SLC17A7, solute carrier family 17 member 7; and SLC17A6, solute carrier family 17 member 6) and moderate levels of a GABAergic neuron marker (SLC6A1, solute carrier family 6 member 1).

Organoids at 5-6 weeks in culture were further analyzed for global gene expression using whole transcriptome shotgun sequencing analysis (RNA-Seq). In this time frame the organoids showed prominent expression of gene markers for neural stem/progenitor cells as well as for the gene coding for the Zika virus receptor protein (FIG. 4). There was also evidence of expression of gene markers for major brain cell lineages including neurons, oligodendrocytes, astrocytes, and polydendrocytes (FIG. 5). Relatively high expression of dopaminergic neuron markers characteristic of a midbrain phenotype were prominently demonstrated and included markers for both A9 (Girk2) and A10 (calbindin) dopaminergic neurons (FIGS. 6 & 10). Organoids also showed moderate to high levels of expression of gene markers previously shown to be associated with positive engraftment outcomes for neural cell transplants to treat rodents with induced Parkinsonism and relatively lower levels of gene expression for markers associated with negative outcomes (FIG. 7). Organoids showed little expression of gene markers for brain regions outside of the caudal midbrain (A9 dopaminergic neurons are located in caudal midbrain) including forebrain, diencephalon, or rostral midbrain markers and low to moderate expression of markers for hindbrain (a region just caudal to the caudal midbrain) (FIG. 8). Additionally, gene expression markers at low to moderate levels were also found for cholinergic, glutaminergic, and gamma-amino butyric acid (GABAergic) neurons, with little or no expression of gene markers for serotonergic neurons (an undesirable cell type for mid-brain transplants) (FIG. 9).

Example 2

Organoids were produced from CS1 cells using the methods of Example 1 and cultured for 5 months. Organoids were then dis-aggregated to produce a population of individualized cells as follows: Organoids were rinsed in PBS then treated with 2 mL 0.05% Trypsin-EDTA (Life Technologies; Carlsbad, CA) for 2 minutes at 37° C. An additional 2 mL Trypsin-EDTA supplemented with 400 µg DNaseI (Millipore-Sigma, Burlington, MA) was added and the cells were mechanically dissociated using a P1000 pipette. The organoids were then incubated for 5 minutes at 37° C. after which, cells were mechanically dissociated using a 1 cc syringe plunger over a 100 µm filter (BD Biosciences; San Jose, CA) washing with cold Hank's Balanced Salt Solution (HBSS; Life Technologies, Carlsbad, CA) to bring the final volume to 25 mL. The cells were centrifuged at 350×G for 3 minutes at 4° C. The resulting supernatant was removed and cell pellet resuspended in 1 mL cold HBSS for counting using a hemocytometer. The cells were centrifuged a third time and resuspended at a concentration of roughly 5×10+ cells per µL of cold HBSS. The final cell solution was counted and viability was assessed using a Trypan Blue exclusion method. The final cell count was calculated as the total number of viable cells per µL. The organoid-derived cell population was then plated on MATRIGEL-coated coverslips and cultured in Neurobasal Medium (Thermo Fisher Scientific, Waltham, MA) with B-27 supplement (Thermo Fisher Scientific, Waltham, MA).

Figure 11A:
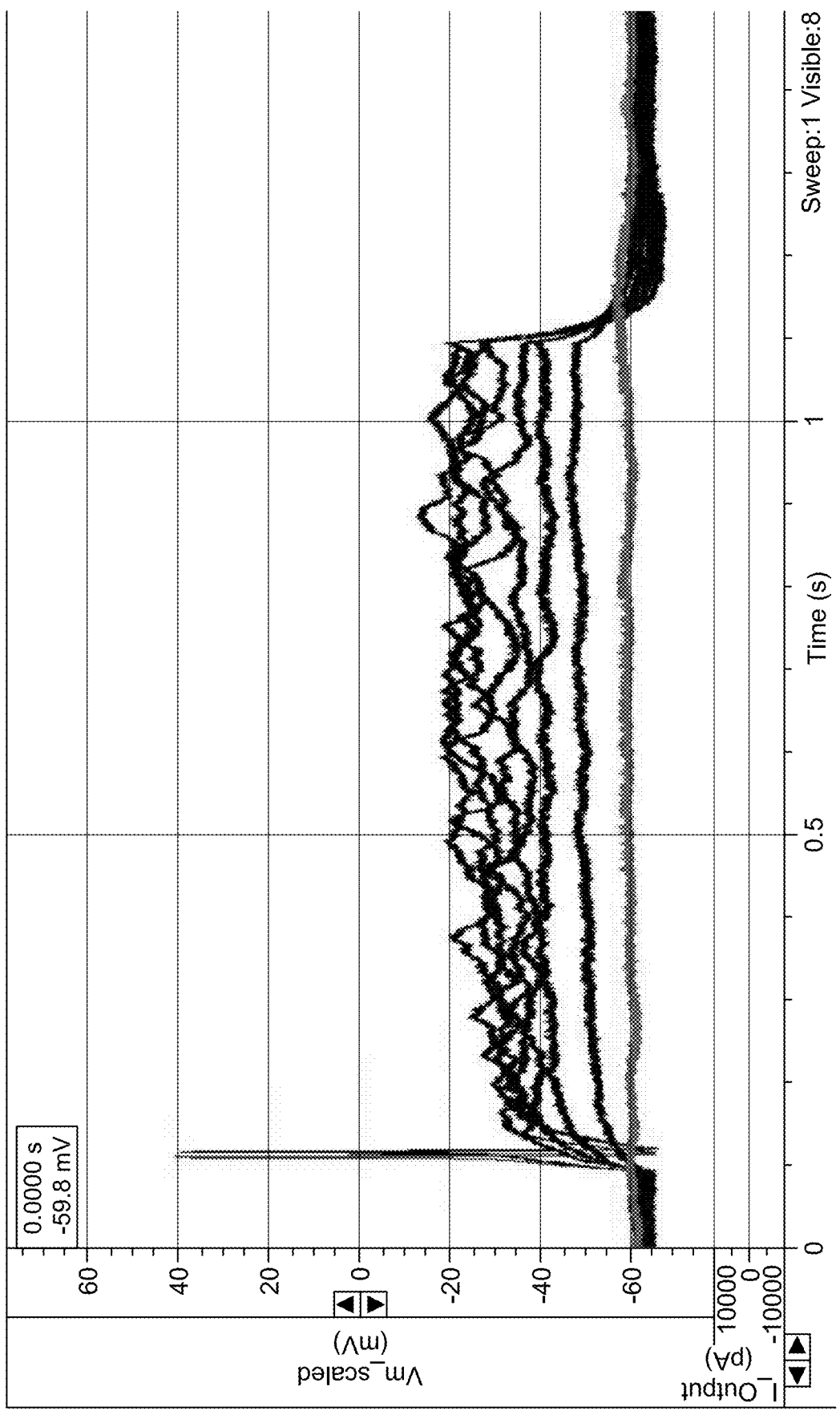
FIG. 11A-FIG. 11C show an exemplary patch-clamp study of neuronal electrophysiology of neurons derived from an organoid derived as described in Example 2.
Figure 11B:
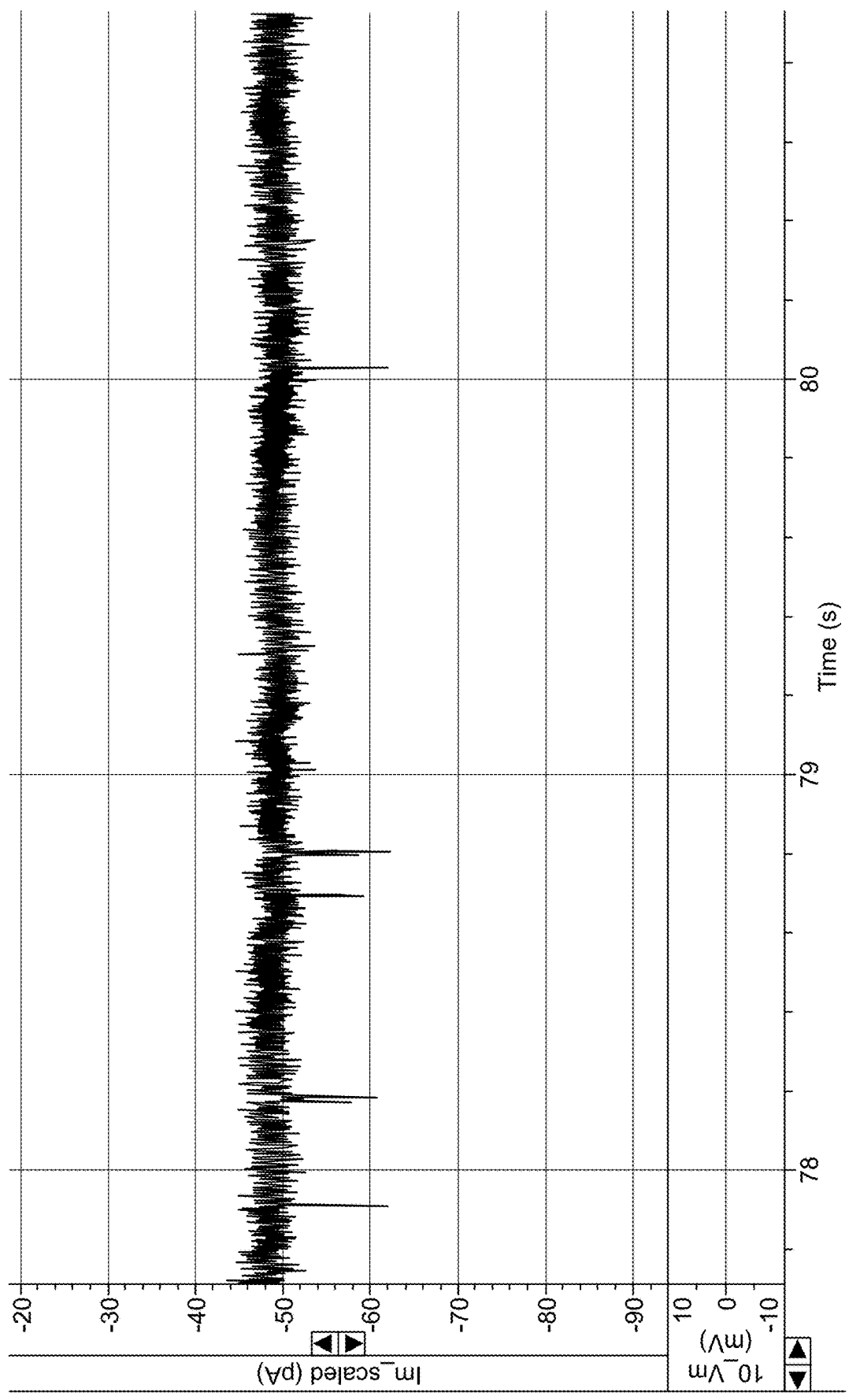
Figure 11C:
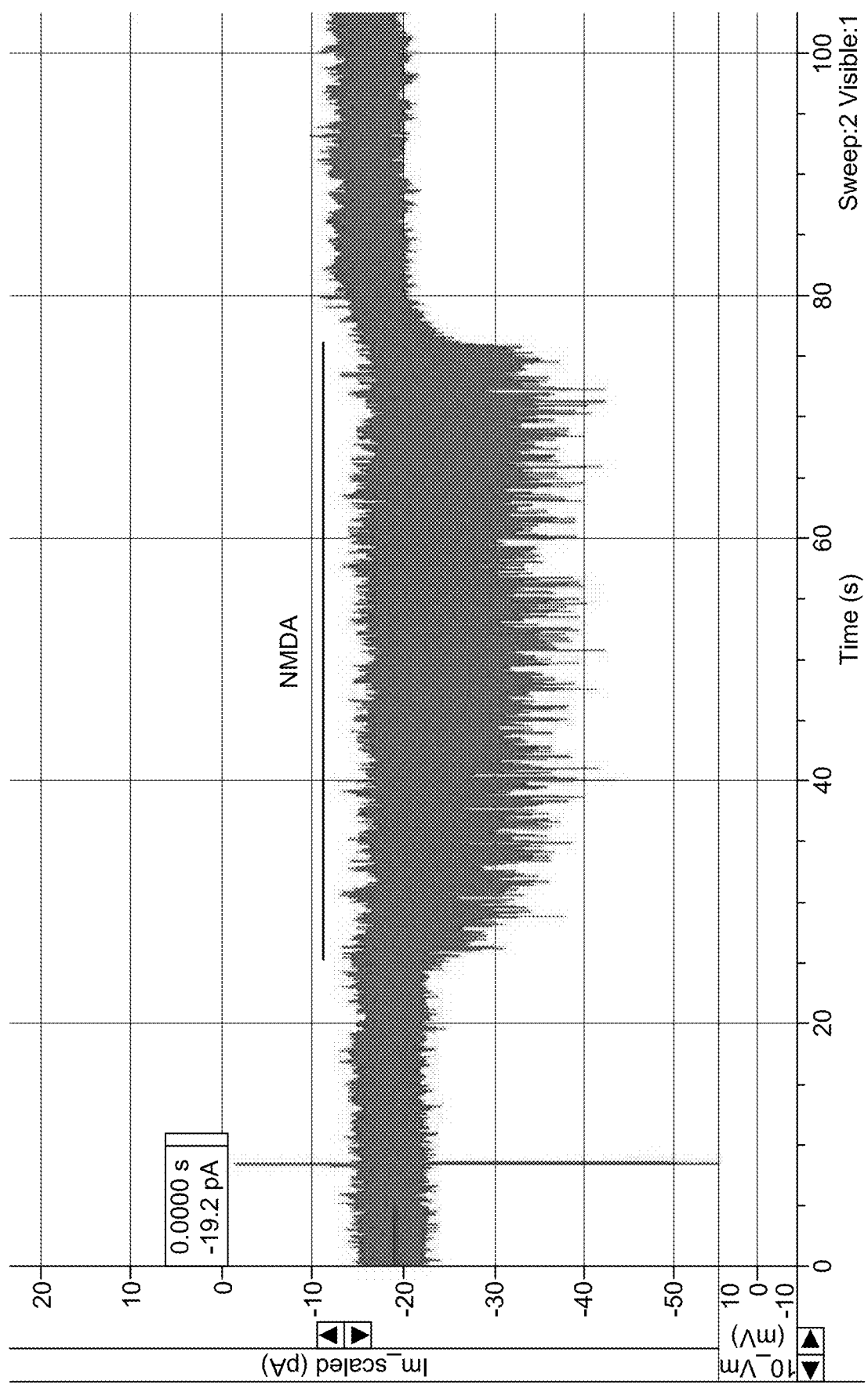

A patch-clamp study of these cell preparations was conducted; results are shown in FIG. 11. FIG. 11A shows a single neuron's (normal) response to electrical stimulation. FIG. 11B shows spontaneous electrical activity of a neuron indicating that it is in contact with other neurons which are stimulating it to respond. FIG. 11C shows neuron responses to NMDA indicating the presence of glutaminergic neurons.

Example 3

Figure 12:
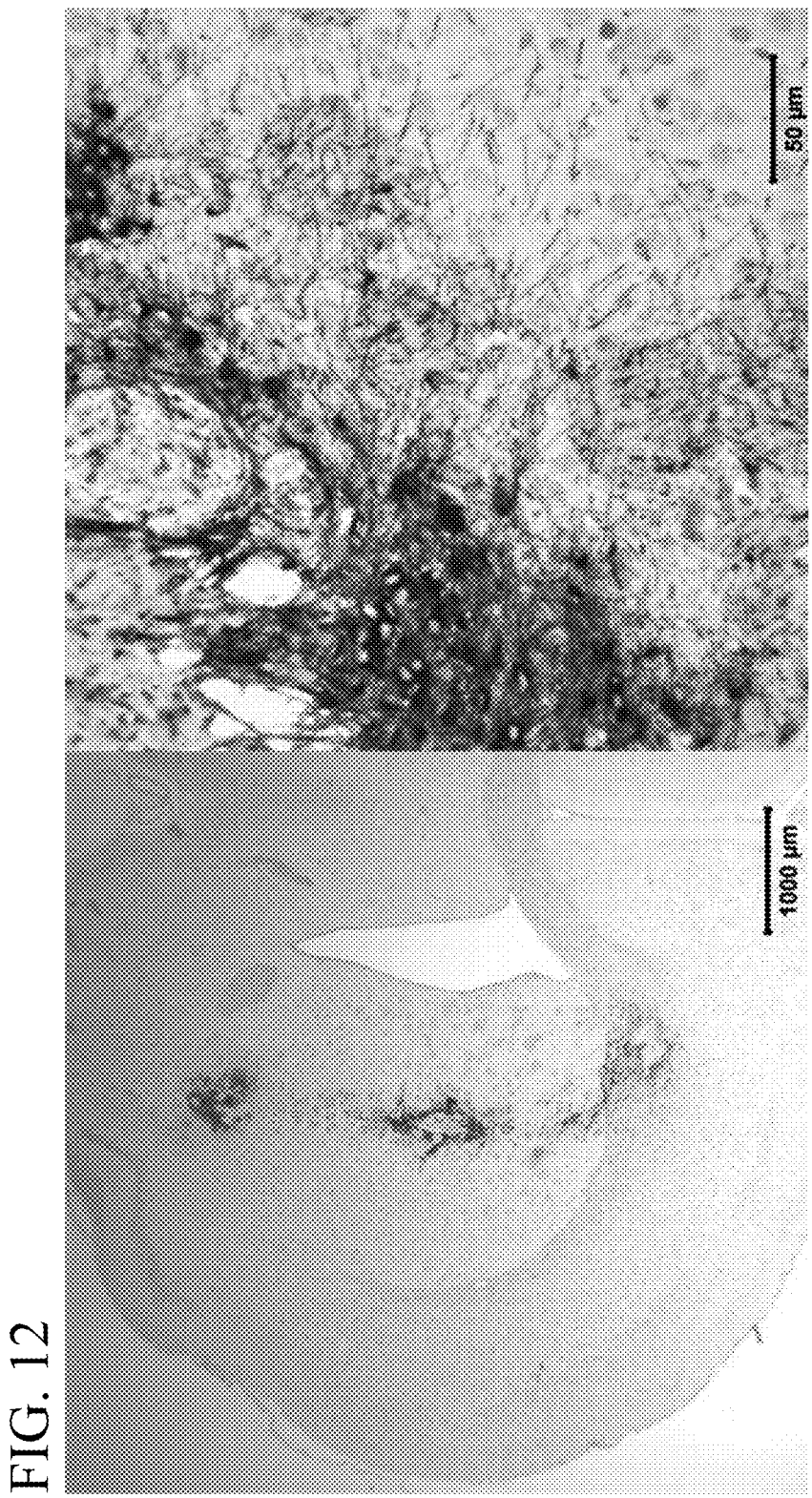
FIG. 12 shows exemplary tissue sections. Nude rat brain (striatum) was transplanted with 300,000 cells derived from 8-week organoids. Four months later, tissue sections were prepared. Immunohistochemistry using a human-specific STEM121 monoclonal antibody demonstrated robust engraftment of human cells four months post-transplantation.

Nude rat brain (striatum) transplanted with 300,000 cells derived from 10-week organoids produced from CS1 or 1024 cells using the methods of Example 1 and using the organoid dis-aggregation method in Example 2. Four months later, tissue sections were prepared and stained for human-specific STEM121; results are shown in FIG. 12. Robust engraftment of the cells at four months post-transplantation was observed.

Example 4

Figure 13:
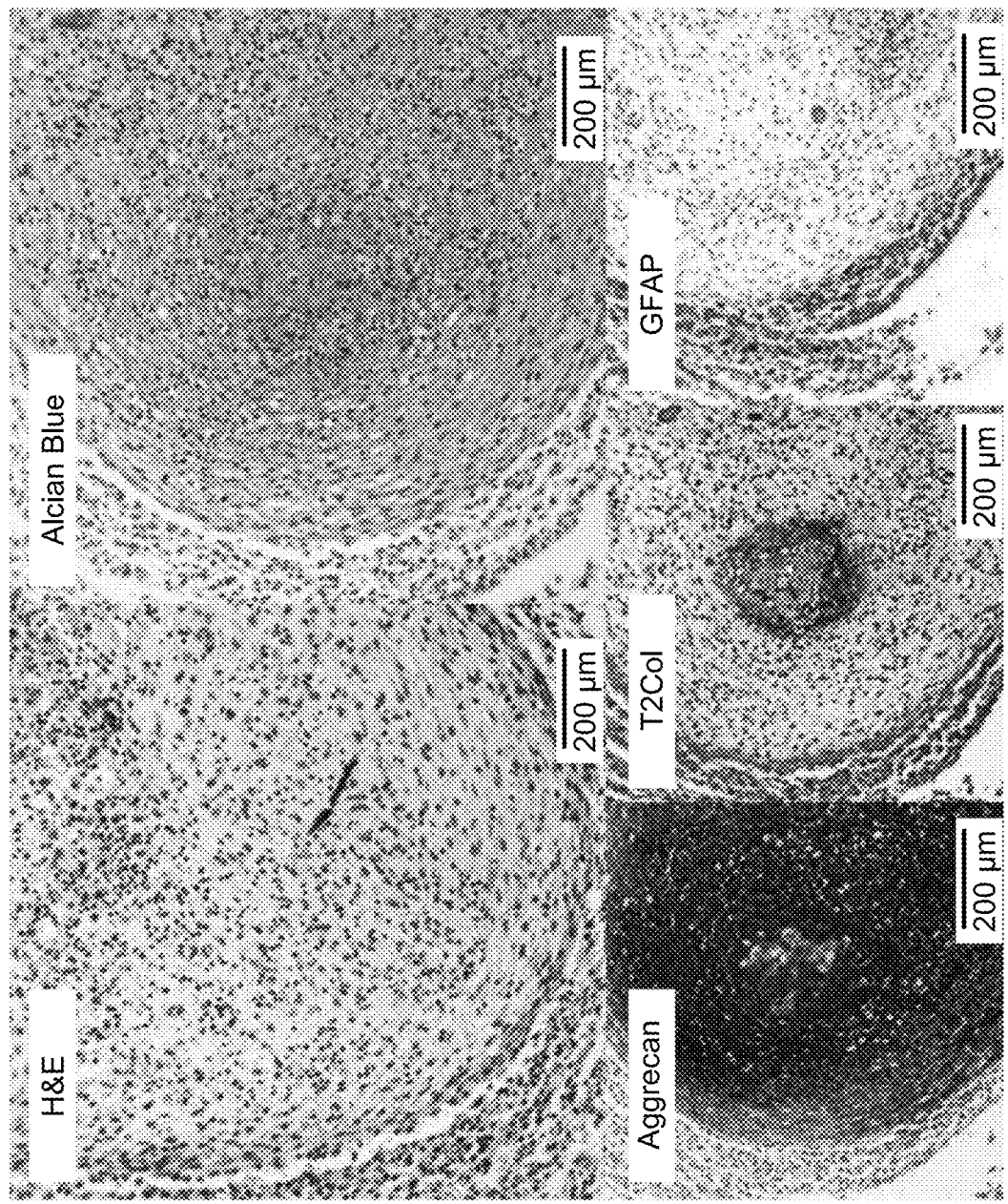
FIG. 13 shows histology of an exemplary organoid demonstrating both cartilage and astrocyte differentiation. Sections stained with haemotoxylin and eosin (H&E) or alcian blue show typical cartilage morphology with chondrocytes surrounded by abundant glycosaminoglycan-rich (blue on alcian blue stain) extracellular matrix and expressing markers typical of cartilage (aggrecan and type 2 collagen, T2Col). Cells adjacent to the cartilage express GFAP, a marker characteristic of astrocytes.
Figure 14:
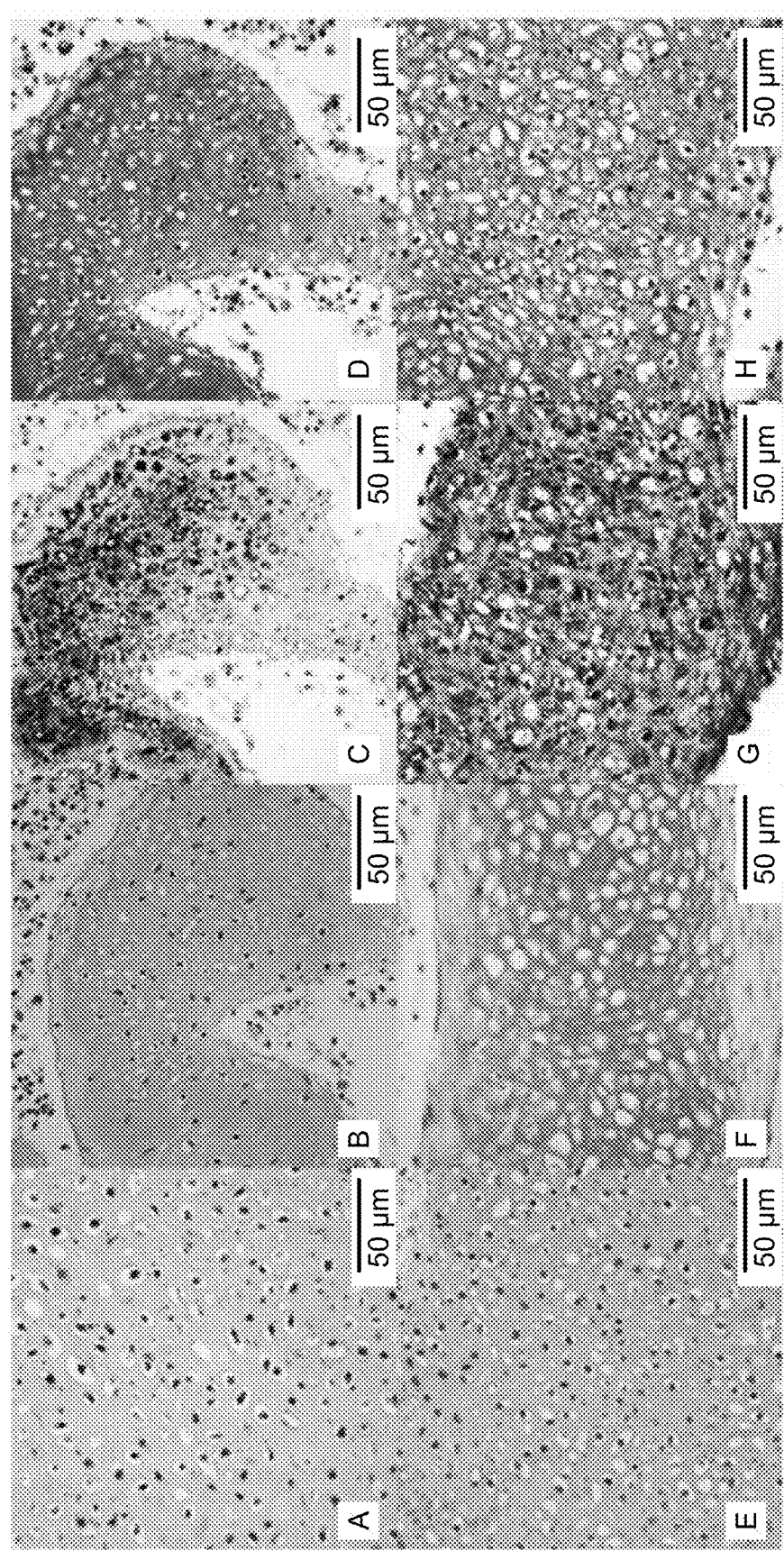
FIG. 14 shows the histology of organoid-generated hyaline cartilage from a cell line after 30 weeks in culture (cell line #1, Panels A-D) or after 12 weeks in culture (cell line #2, Panels E-H). Panel A & Panel E show H&E stained sections, demonstrating typical hyaline cartilage morphology with chondrocytes surrounded by abundant matrix. Panel B & Panel F show alcian blue staining, demonstrating positive (blue) staining typical of cartilaginous matrix. Panel C & Panel G show immunohistochemical stains for aggrecan, consistent with hyaline cartilage. Panel D & Panel H show immunohistochemical stains for type 2 collagen, consistent with hyaline cartilage. Size bars=50 µm.
Figure 15:
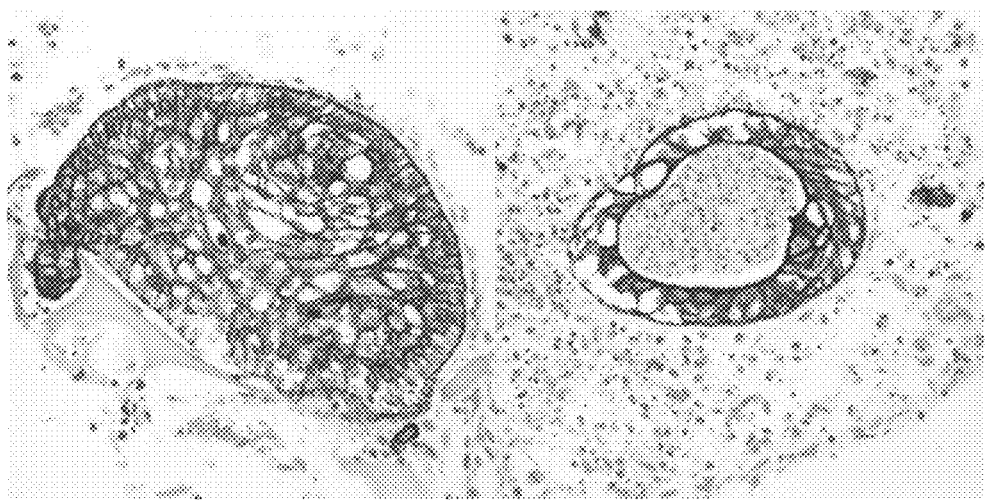
FIG. 15 shows histological analysis of exemplary organoids from iPSC line CS1 after 9 weeks of culture in ESSENTIAL 8 medium in G-Rex 100 cell culture flasks. The organoids show development of epithelial structures with positive staining for wide-spectrum cytokeratins (ws-CK). Staining was performed using ws-CK IHC stains.

Human iPSCs were induced to form organoids, as described in Example 1 using a chemically-defined hydrogel (Cell-Mate3D, BRTI Life Sciences, Two Harbors, MN) and ESSENTIAL 8 medium (E8, Thermo Fisher Scientific Life Sciences). The resulting organoids were then maintained in long-term cell culture (for example, 7 weeks to 7 months) in GREX flasks (GREX, Wilson Wolf Inc., New Brighton, MN). A loss of neural elements and transition to tissue comprised mainly of hyaline cartilage was observed, as shown in FIG. 13, and FIG. 14.

Figure 16:
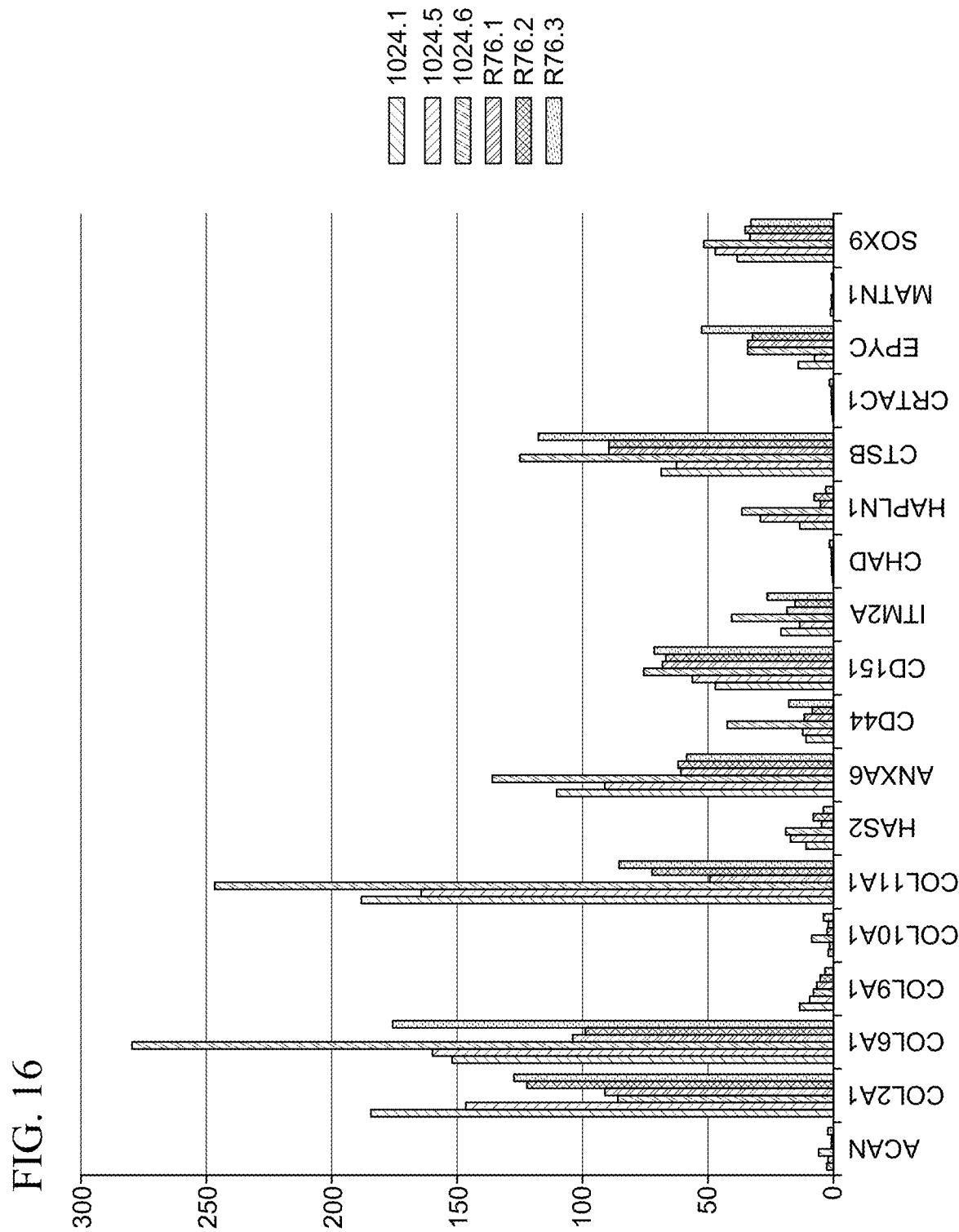
FIG. 16 shows RNA-Seq gene expression analysis of pooled, 5-6 week organoids derived from 2 different iPSC lines (1024 & R76) with 3 biological replicates of each. This panel shows expression of genes that are markers of chondrocytes including aggrecan (ACAN), type II collagen (COL2A1), Type VI collagen (COL6A1), type IX collagen (COL9A1), type X collagen (COL10A1), type XI collagen (COL11A1), hyaluronan synthase (HAS2), annexin A6 (ANXA6), CD44 molecule (CD44), CD151 molecule (CD151), integral membrane protein 2A (ITM2A), chondroadherin (CHAD), link protein 1 (HAPLN1), cathepsin B (CTSB), cartilage acidic protein 1 (CRTAC1), epiphycan (EPYC), matrilin 1 (MATN1), and SRY-Box 9 (SOX9).

These cells were also observed to express of genes that are markers chondrocytes, as shown in FIG. 16.

Example 5

Human iPSCs were induced to form organoids, as described in Example 1 using a chemically-defined hydrogel (Cell-Mate3D, BRTI Life Sciences, Two Harbors, MN) and ESSENTIAL 8 medium (E8, Thermo Fisher Scientific Life Sciences). The resulting organoids were then maintained in long-term cell culture for 9 weeks in ESSENTIAL 8 media in GREX flasks (GREX, Wilson Wolf Inc., New Brighton, MN). Development of epithelial structures with positive staining for wide-spectrum cytokeratins was observed.

Example 6

Cell Culture with Cell-Mate3D uGel 40

The steps of Cell Culture with Cell-Mate3D, as described in Example 1, were performed with the following modifications, beginning at step 8:

8. Aspirate supernatant and resuspend cell pellet in 40 μL of Cell-Mate3D uGel hydration fluid (Catalog No. CM-401, BRTI Life Sciences, Two Harbors, MN).
9. Add hydration fluid suspension to dry construct, according to manufacturer's protocol.
10. Wait five minutes for absorption and transfer Cell-Mate3D uGel to prepared Wilson Wolf flask.
11. Culture cells in a 37° C. incubator (5% $CO_2$, 20% $O_2$); change media every 3-4 days.

Example 7

Human iPSCs were induced to form organoids, as described in Example 1 or 6 using a chemically-defined hydrogel (Cell-Mate3D, BRTI Life Sciences, Two Harbors, MN) and ESSENTIAL 8 medium (E8, Thermo Fisher Scientific Life Sciences). Alternatively, human iPSCs were induced to form organoids as described in Example 1 or 6 but a buffered hyaluronic acid (HA) solution was added for 12-24 hours instead using the hydrogel; following HA treatment the iPSCs were transferred directly to ESSENTIAL 8 media in the GREX bioreactor flasks. The resulting hydrogel-generated multi-tissue organoids (MTOs) or hyaluronic acid-generated MTOs were then maintained in long-term cell culture for 12 weeks or 30 weeks in ESSENTIAL 8 media in GREX flasks (GREX, Wilson Wolf Inc., New Brighton, MN).

Figure 17:
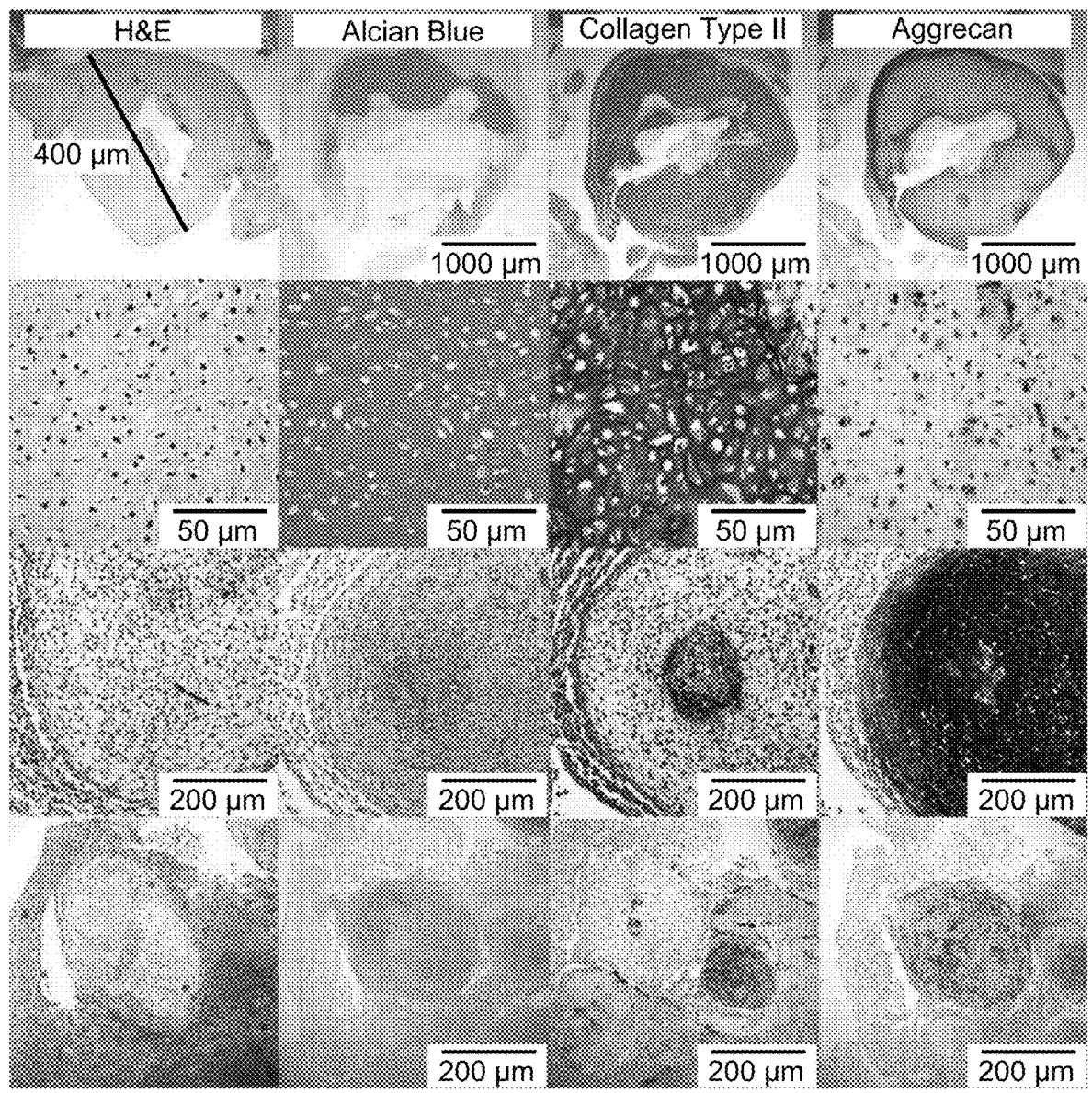
FIG. 17 shows histology of organoids prepared as described in Example 7. Rows 1 & 2 show hydrogel-generated multi-tissue organoids (MTOs) after 30 weeks in culture. These organoids show mature hyaline cartilage morphology with chondrocytes surrounded by abundant matrix with typical Alcian blue staining (column 2). IHC stains for aggrecan (column 4) and type II collagen (column 3) are consistent with hyaline cartilage. Size bars on first row=1000 µm, and measure bar on top row H&E image=4,363 µm (4.363 mm). Row 3 shows developing cartilage in hydrogel-generated MTO at 12 weeks. Row 4 shows developing cartilage in hyaluronic acid-generated MTO at 12 weeks.

Cartilage/chondrocytes were present in the resulting multi-tissue organoids (MTOs). As shown in FIG. 17, developing hyaline cartilage was apparent after 12 weeks in both hyaluronic acid-generated MTO and hydrogel-generated MTO. After 30 weeks, mature hyaline cartilage morphology with chondrocytes surrounded by abundant matrix was observed and immunohistochemical (IHC) staining for aggrecan and type II collagen was consistent with hyaline cartilage.

Example 8

Human iPSCs were induced to form hydrogel-generated MTOs, as described in Example 7. The resulting organoids were then maintained in long-term cell culture for 12 weeks in ESSENTIAL 8 media in GREX flasks (GREX, Wilson Wolf Inc., New Brighton, MN).

Cartilage/chondrocytes were isolated from the resulting organoids using digestion with trypsin/DNase, using one of the following methods:

2-stage chondrocyte isolation: MTOs were rinsed in PBS and suspended in 2 mL trypsin (0.025%, Sigma Aldrich) for 2 minutes at 37° C. Next, using a scalpel MTO are mechanically disrupted in DNAse1/0.025% trypsin, incubated for 5 minutes at 37° C. and dissociated with cold Hank's Balanced Salt Solution (HBSS; Life Technologies) over a 100 μm filter (BD Biosciences, San Jose, CA). Cartilage tissue retained on the filter is back-flushed with 25 ml of cold HBSS, collected, and further disaggregated to single cell preparations in 2 mL of collagenase II/DNase (Celase GMP, Worthington Biochemical Corporation, Lakewood, NJ) for 10 minutes at 37° C. The cell pellet is resuspended in cold HBSS, centrifuged again and resuspended in HBSS, counted, and its viability assessed using Trypan blue.

1-stage chondrocyte isolation: MTOs in the bioreactor are rinsed in PBS and resuspended in 12 mL trypsin (0.025%, Sigma Aldrich) with 600 μg DNAse1 with gentle agitation for 30-60 minutes (until a majority of the tissue fragments are broken down to single cells) at 37° C. The cells are then collected and the pellet resuspended in cold HBSS, centrifuged again and resuspended in HBSS, counted, and viability assessed.

Figure 18:
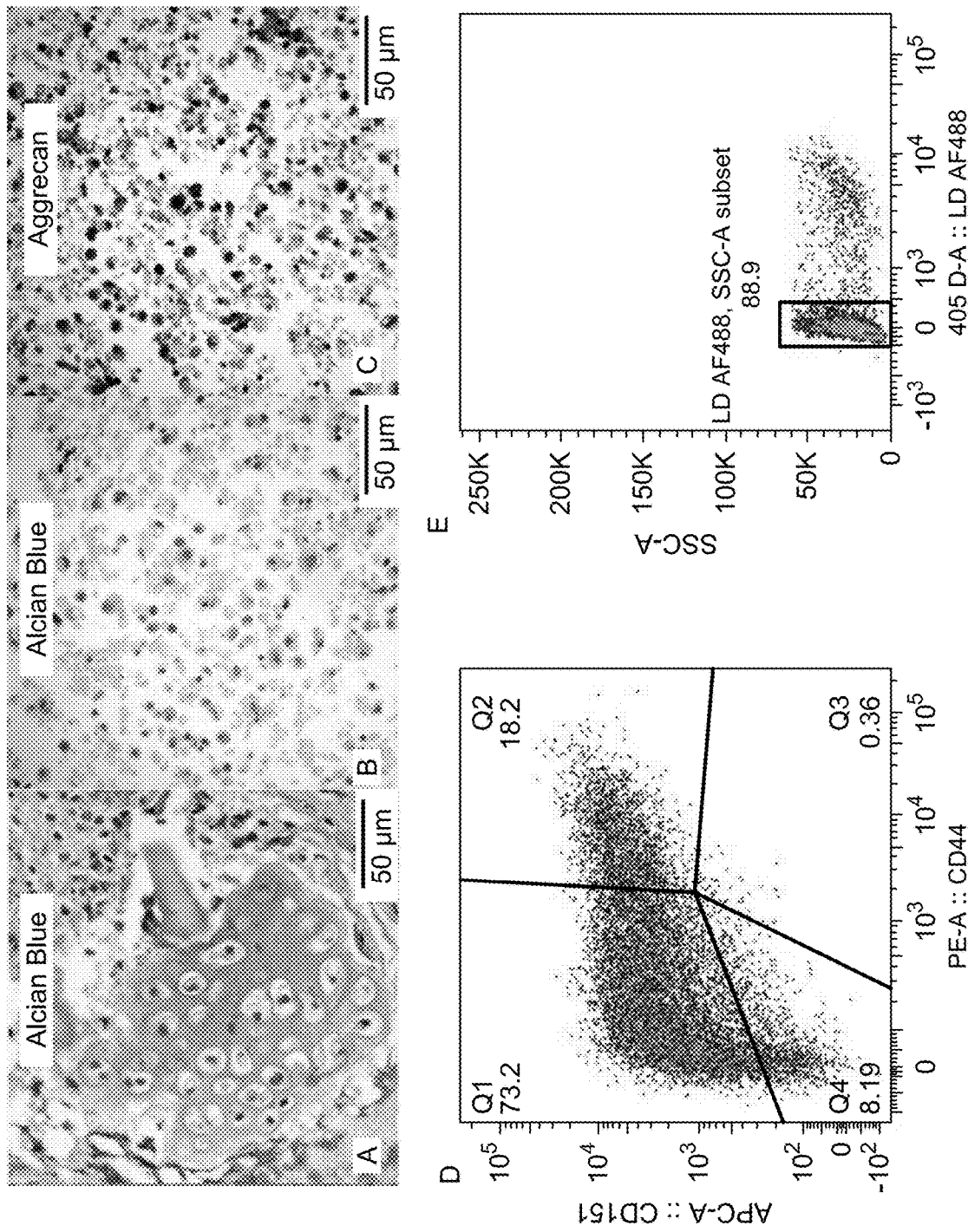
FIG. 18 shows cartilage/chondrocyte isolation from MTOs at 12 weeks using a 2-stage chondrocyte isolation, as described in the Examples. Panel A shows tissue captured on a 100 µm filter following digestion of MTOs with trypsin/DNase, showing partially digested pieces of hyaline cartilage and isolated chondrocytes. Panels B & C show chondrocytes isolated from tissue captured by the 100 µm filter following digestion with type II collagenase. The majority of isolated cells show Alcian blue staining, with aggrecan labeling in a large subpopulation, consistent with a cell population comprised predominantly of chondrocytes. Size bars=50 µm. Panels D & E show flow cytometry analysis of a total population of 80 million cells isolated using a 2-stage chondrocyte isolation; 18% of cells exhibit double labeling for chondrocyte markers CD44 and CD151 (Panel D) and 88.9% viability (Panel E).

Exemplary results of the 2-stage chondrocyte isolation are shown in FIG. 18.

Figure 19:
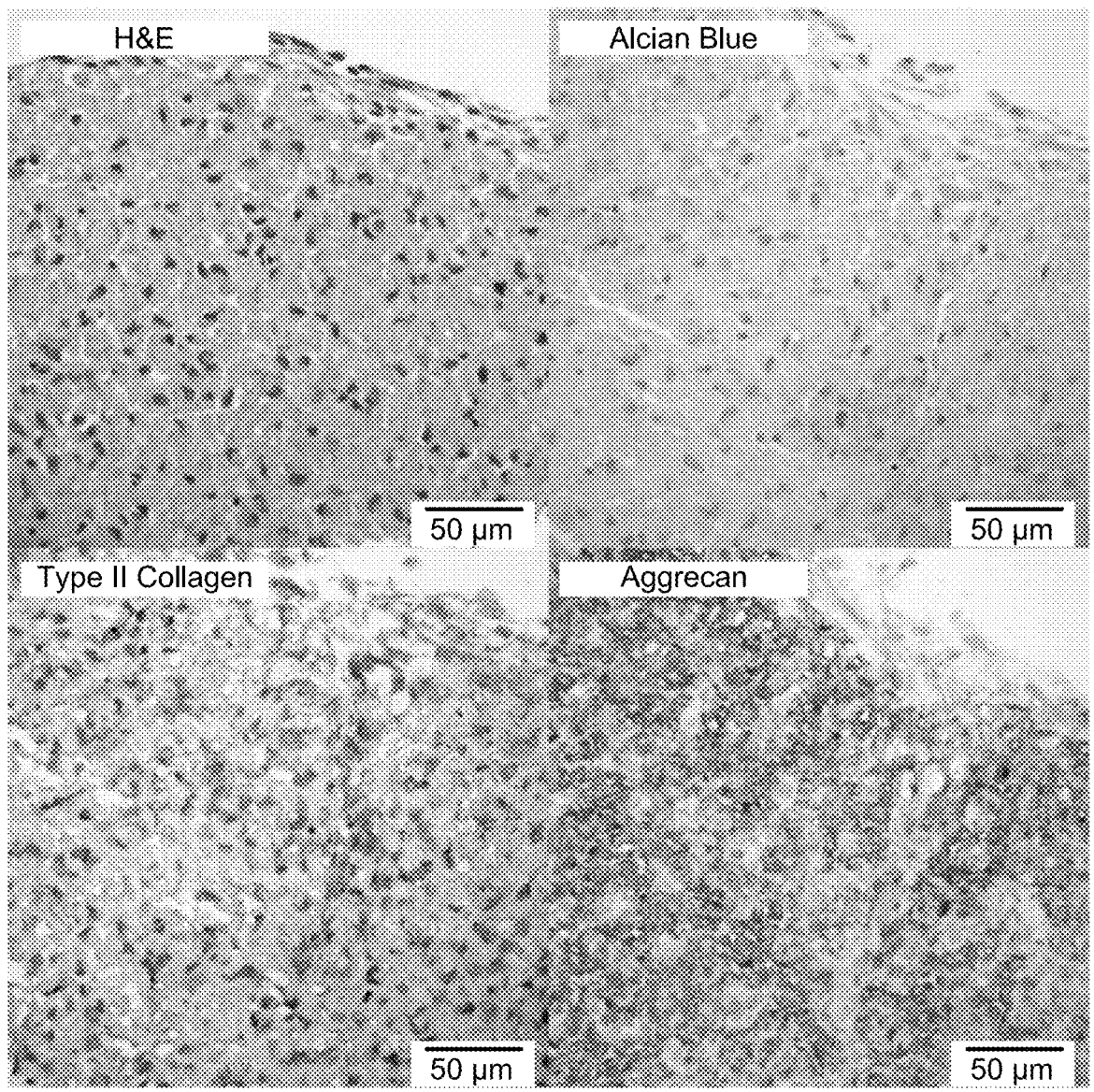
FIG. 19 shows histological analysis of isolated MTO-generated human chondrocytes placed in an ultralow attachment plate in chondrogenic medium for 1 month during which they self-assembled into spherical aggregates. The resulting spherical aggregates show extensive chondrogenesis with production of Alcian blue staining matrix (upper right panel), early type II collagen deposition (lower left panel), and extensive aggrecan expression (lower right panel). H&E staining is shown in the upper left panel. Size bars=50 µm.

After isolation, the cells were placed in an ultra-low attachment plate (Corning Ultra-Low Attachment Surface, 6-well plates, obtained from Millipore Sigma) in ESSENTIAL 8 media (E8, Thermo Fisher Scientific Life Sciences) for 1 month. As shown in FIG. 19, the cells self-assembled into spherical aggregates. These spherical aggregates exhibited extensive chondrogenesis with production of an Alcian blue staining matrix, early type II collagen deposition, and extensive aggrecan expression.

The complete disclosure of all patents, patent applications, and publications, and electronically available material (including, for instance, nucleotide sequence submissions in, for example, GenBank and RefSeq, and amino acid sequence submissions in, for example, SwissProt, PIR, PRF, PDB, and translations from annotated coding regions in GenBank and RefSeq) cited herein are incorporated by reference. In the event that any inconsistency exists between the disclosure of the present application and the disclosure(s) of any document incorporated herein by reference, the disclosure of the present application shall govern. The foregoing detailed description and examples have been given for clarity of understanding only. No unnecessary limitations are to be understood therefrom. The invention is not limited to the exact details shown and described, for variations obvious to one skilled in the art will be included within the invention defined by the claims.

What is claimed is:
1. A method comprising:
introducing an induced pluripotent stem cell (iPSC) into a cell culture medium lacking a three-dimensional matrix, the culture medium comprising:
a chemically defined maintenance cell culture medium, and
hyaluronic acid in an amount effective to induce the iPSC to differentiate; and
transferring the iPSC and culture medium to a non-microfluidic bioreactor, the bioreactor comprising a non-adherent culture without the use of a three-dimensional matrix;
culturing the iPSC in the bioreactor for at least 1 week at a temperature from 32° C. to 40° C.; and
producing a three-dimensional multi-tissue organoid comprising cartilage, bone, fibrous connective tissue, brain tissue, or epithelial tissue, or a combination thereof.

2. The method of claim 1, wherein the cell culture medium further comprises one or more of fibroblast growth factor 2 (FGF2), transforming growth factor beta (TGFβ), chitosan, growth differentiation factor 5 (GDF-5), and bone morphogenetic protein 2 (BMP-2).

3. The method of claim 1, wherein the organoid comprises one or more of an oligodendrocyte, an astrocyte, a polydendrocyte, a neural precursor cell, a neural stem cell, a neural progenitor cell, a neural crest cell, a chondrocyte, a cytokeratin-expressing epithelial cell, a type 1-collagen-expressing cell, an osteocyte, a mesenchymal stem cell, or a skeletal stem cell, or a derivative thereof, or a mixture thereof.

4. The method of claim 1, wherein the organoid comprises bone, fibrous connective tissue, or epithelial tissue, or a combination thereof.

5. The method of claim 1, the method further comprising obtaining the iPSC from a culture plate prior to introducing the iPSC into the culture medium comprising hyaluronic acid.

6. The method of claim 1, wherein the bioreactor comprises a second cell culture medium.

7. The method of claim 1, wherein culturing the iPSC in the bioreactor comprises culturing the cell at 37° C.

8. The method of claim 1, wherein culturing the iPSC in the bioreactor comprises culturing the iPSC in hypoxic conditions.

9. The method of claim 1, the organoid comprising:
   a cell expressing glial fibrillary acidic protein (GFAP);
   a cell expressing microtubule associated protein 2 (MAP2);
   a cell expressing myelin basic protein (MBP);
   a cell expressing type 1 collagen (T1Col);
   a cell expressing type 2 collagen (T2Col);
   a cell expressing aggrecan; or
   or a cell expressing cytokeratins,
   or a combination thereof.

10. The method of claim 1, the method further comprising dis-aggregating cells of the organoid to produce a population of individualized cells.

11. The method of claim 10, the method further comprising culturing a cell from the population of individualized cells.

12. The method of claim 1, wherein the method further comprises isolating a chondrocyte from the organoid.

13. The method of claim 12, wherein the method further comprises forming a chondrocyte aggregate.

14. The method of claim 12, wherein the method further comprises culturing the chondrocyte on an ultra-low attachment surface or in a chondrogenic media, or both.

15. The method of claim 1 wherein the cartilage is type 2 collagen (T2Col)-expressing cartilage.

\* \* \* \* \*

UNITED STATES PATENT AND TRADEMARK OFFICE
CERTIFICATE OF CORRECTION

PATENT NO. : 12,139,722 B2
APPLICATION NO. : 17/344064
DATED : November 12, 2024
INVENTOR(S) : Timothy D. O'Brien et al.

Page 1 of 1

It is certified that error appears in the above-identified patent and that said Letters Patent is hereby corrected as shown below:

In the Claims

In Column 24, Line 1 (Claim 9): the word 'or' should be removed.

Signed and Sealed this
Eleventh Day of March, 2025

Coke Morgan Stewart
*Acting Director of the United States Patent and Trademark Office*